(12) United States Patent
Li et al.

(10) Patent No.: US 8,367,899 B2
(45) Date of Patent: Feb. 5, 2013

(54) GRAY LEAF SPOT TOLERANT MAIZE AND METHODS OF PRODUCTION

(75) Inventors: Bailin Li, Hockessin, DE (US); William A. Wilson, Noblesville, IN (US)

(73) Assignees: E I du Pont de Neumours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 787 days.

(21) Appl. No.: 12/336,624

(22) Filed: Dec. 17, 2008

(65) Prior Publication Data

US 2009/0172845 A1    Jul. 2, 2009

Related U.S. Application Data

(60) Provisional application No. 61/009,697, filed on Dec. 31, 2007.

(51) Int. Cl.
  *A01H 1/00* (2006.01)
  *A01H 1/02* (2006.01)
  *A01H 5/10* (2006.01)
  *A01G 5/00* (2006.01)
  *C12N 5/04* (2006.01)

(52) U.S. Cl. ............ 800/320.1; 800/260; 800/278; 800/279; 800/295; 800/275; 800/265; 800/266; 800/300.1; 435/412; 435/424; 435/6.1

(58) Field of Classification Search ............ None
See application file for complete search history.

(56) References Cited

U.S. PATENT DOCUMENTS

| | | | |
|---|---|---|---|
| 5,567,861 A | 10/1996 | Niebur | |
| 5,574,210 A | 11/1996 | Saghai-Maroof et al. | |
| 5,942,670 A | 8/1999 | Whitaker | |
| 2009/0064360 A1 | 3/2009 | Kerns et al. | |
| 2009/0064361 A1 | 3/2009 | Butruille et al. | |

FOREIGN PATENT DOCUMENTS

WO    2008042185    4/2008

OTHER PUBLICATIONS

Bubeck et al., 1993. Quantitative Trait Loci Controlling Resistance to Gray Leaf Spot in Maize. Crop Science vol. 33, p. 838-847.
Saghai-Maroof M.A. et al., 1996. Identification of Quantitative Trait Loci Controlling Resistance to Gray Leaf Spot Disease in Maize. Theor. Appl. Genet. vol. 93, p. 539-546.
Wisser et al., 2006. The Genetic Architecture of Disease Resistance in Maize: A Synthesis of Published Studies. Phytopathology vol. 96(2), p. 120-129.
Shi Liyu, 2007. Comparative QTL Mapping of Resistance to Gray Leaf Spot in Maize Based on Bioinformatics. Agricultural Sciences in China, vol. 6(12), p. 1411-1419.
Gordon et al., 2004. Linkage of Molecular Markers to *Cercospora zeae-maydis* Resistance in Maize. Crop Science, vol. 44(2), p. 628-636.
Lehmensiek et al., 2001. Genetic Mapping of Gray Leaf Spot (GLS) Resistance Genes in Maize. Theoretical and Applied Genetics, vol. 103(5), p. 797-803.
Clements et al., 2000. Quantitative Trait Loci Associated with Resistance to Gray Leaf Spot of Corn. Phytopathology, vol. 90(9), p. 1018-1025.
Danson et al., 2008. Quantitative Trait Loci (QTLs) for Resistance to Gray Leaf Spot and Common Rust Diseases of Maize. African Journal of Biotechnology, vol. 7(18), p. 3247-3254.
Balint-Kurti et al., 2008. Use of an Advanced Intercross Line Population for Precise Mapping of Quantitative Trait Loci for Gray Leaf Spot Resistance in Maize. Crop Science, vol. 48(5), p. 1696-1704.
Pereira et al., 2000. QTL Mapping and Disease Resistance in Cereals. Journal of New Seeds, vol. 2(2), p. 1-21.
Database MaizeGDB, XP002518440, Accession No. UMC1346, published Nov. 13, 1999.
Database MaizeGDB, XP002518441, Accession No. UMC1299, published Nov. 9, 1999.
Database MaizeGDB, XP002518442, Accession No. UMC1702, published Jul. 31, 2000.
Database MaizeGDB, XP002518443, Accession No. BNLG1755, published 1999.
S. T. Coates et al., Sources of Resistance to Gray Leaf Spot of Corn, Plant Disease, American Phytopathological Society, Jan. 1, 1994, pp. 1153-1155, vol. 78, No. 12.
Stuart G. Gordon et al., Heritability and Components of Resistance to *Cercospora zeae-maydis* Derived from Maize inbred VO613Y, Phytopathology, Jun. 2006, pp. 593-598, vol. 96, No. 6.

*Primary Examiner* — Medina A Ibrahim

(57) ABSTRACT

The invention relates to methods and compositions for identifying maize plants that have newly conferred tolerance or enhanced tolerance to, or are susceptible to, Gray Leaf Spot (GLS). The methods use molecular genetic markers to identify, select and/or construct tolerant plants or identify and counter-select susceptible plants. Maize plants that display newly conferred tolerance or enhanced tolerance to GLS that are generated by the methods of the invention are also a feature of the invention.

13 Claims, 16 Drawing Sheets

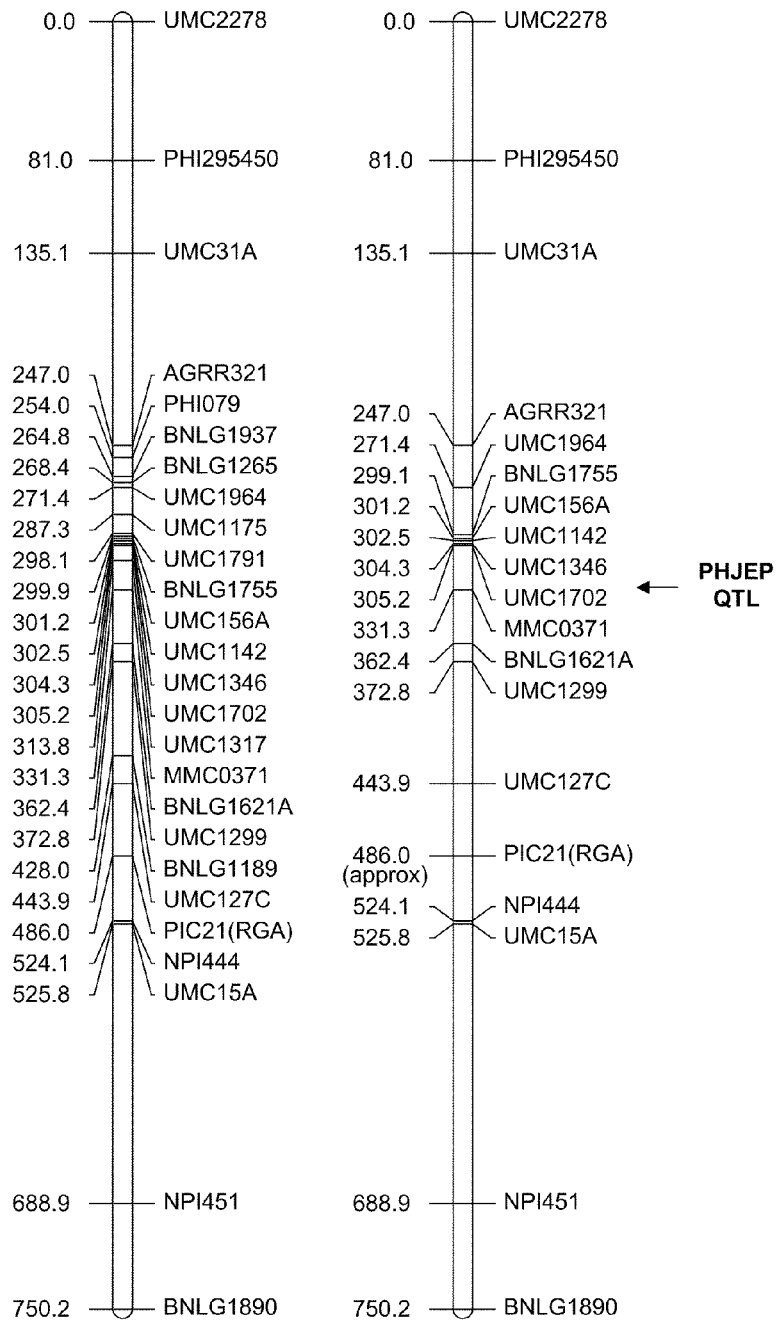
FIG. 1: Final location of PHJEP GLS QTL on IBM2 2004 neighbors chromosome 4 map

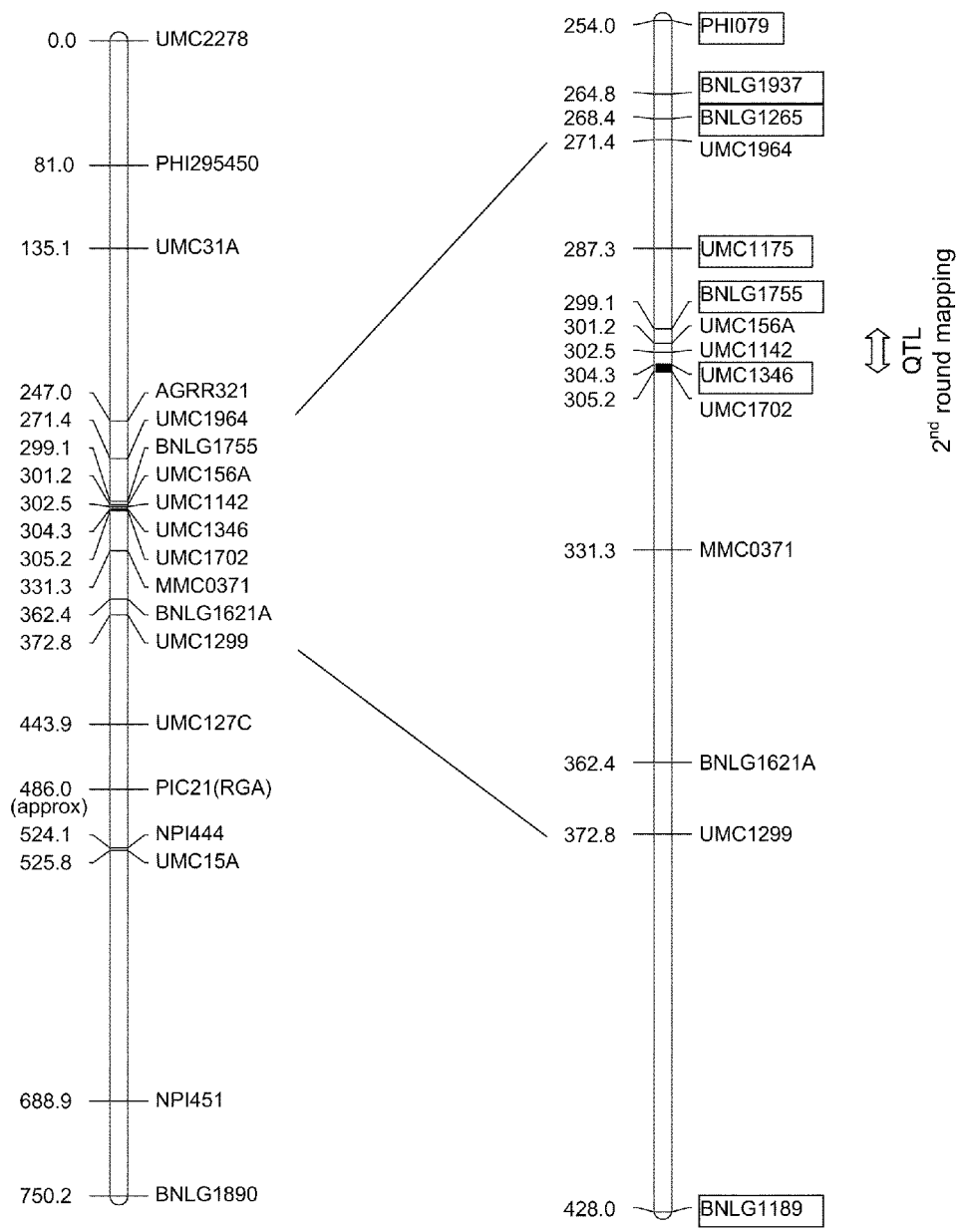
FIG. 2: GLS QTL on IBM2 2004 neighbors chromosome 4 map after second round of mapping

FIG. 3A GLS QTL Map Location

| Locus | QTL | CAPS info | left primer | right primer |
|---|---|---|---|---|
| bacm2.pk027.h10.f | | PCR | SEQ ID NO:1 | SEQ ID NO:2 |
| est635183x | | | | |
| bnlg1755 | | | | |
| mmp140 | | | | |
| bacm.pk098.d7 | | MseI | SEQ ID NO:3 | SEQ ID NO:4 |
| bacm.pk106.j3 | | MspI | SEQ ID NO:5 | SEQ ID NO:6 |
| bacm.pk018.h15 | | AluI | SEQ ID NO:7 | SEQ ID NO:8 |
| bacm.pk040.o17 (PHM 00045) | | BsmAI | SEQ ID NO:9 | SEQ ID NO:10 |
| fae2 | | | | |
| bacm2.pk065.b22.f | | PCR | SEQ ID NO:11 | SEQ ID NO:12 |
| bacb.pk0333.o19 (PHM 00043) | | ScrFI | SEQ ID NO:13 | SEQ ID NO:14 |
| umc1142 | | | | |
| umc1346 | | | | |
| bacc.pk0267.m12.f | | EcoNI | SEQ ID NO:15 | SEQ ID NO:16 |
| cl33021_1 | ■ | MwoI | SEQ ID NO:17 | SEQ ID NO:18 |
| bacb.pk0241.h17.f | ■ | RsaI | SEQ ID NO:19 | SEQ ID NO:20 |
| PHM 15534 | ■ | | | |
| PHM 04694 | ■ | | | |
| chp2.pk0007.d2 | ■ | ScrFI | SEQ ID NO:21 | SEQ ID NO:22 |
| est337054x | ■ | | | |
| csu100(ptk) | ■ | | | |
| bacc.pk0530.f13.f | ■ | MaeII | SEQ ID NO:23 | SEQ ID NO:24 |
| p0094.csstg88 | ■ | TaqI | SEQ ID NO:25 | SEQ ID NO:26 |
| bacb.pk0269.n19 | ■ | PCR | SEQ ID NO:27 | SEQ ID NO:28 |
| Putative R gene | ■ | | | |
| bacb.pk0009.b21.f | ■ | TaqI | SEQ ID NO:29 | SEQ ID NO:30 |
| bacb.pk0117.i09.f | | BsrI | SEQ ID NO:31 | SEQ ID NO:32 |

FIG. 3B GLS QTL Map Location

| Locus | QTL | CAPS info | left primer | right primer |
|---|---|---|---|---|
| PHM 01811 | | | | |
| PHM 01963 | | | | |
| bacc.pk0280.n12 | | PCR | SEQ ID NO:33 | SEQ ID NO:34 |
| bacb.pk0219.j20 | | PCR | SEQ ID NO:35 | SEQ ID NO:36 |
| dup53466x | | | | |
| bacc.pk0132.b16.f | | MaeIII | SEQ ID NO:37 | SEQ ID NO:38 |
| bacb.pk0221.o22 | | NdeI | SEQ ID NO:39 | SEQ ID NO:40 |
| PHM 05013 | | | | |
| PHM 00586 | | | | |
| umc1702 | | | | |
| bacb.pk0544.j18 | | MseI | SEQ ID NO:41 | SEQ ID NO:42 |
| bacb.pk0540.c18.f | | StyI | SEQ ID NO:43 | SEQ ID NO:44 |
| ay110355 | | | | |
| bacm.pk022.b8 (PHM 00049) | | MseI | SEQ ID NO:45 | SEQ ID NO:46 |
| ay110562 | | | | |
| mmc0371 | | | | |
| umc1945 | | | | |
| umc2284 | | | | |
| csu638 | | | | |
| umc156a | | | | |
| PHM 7245 | | PCR | SEQ ID NO:47 | SEQ ID NO:48 |
| umc2391 | | | | |
| csu661 | | | | |
| bnlg1621a | | | | |
| ay110310 | | | | |
| umc1299 | | | | |

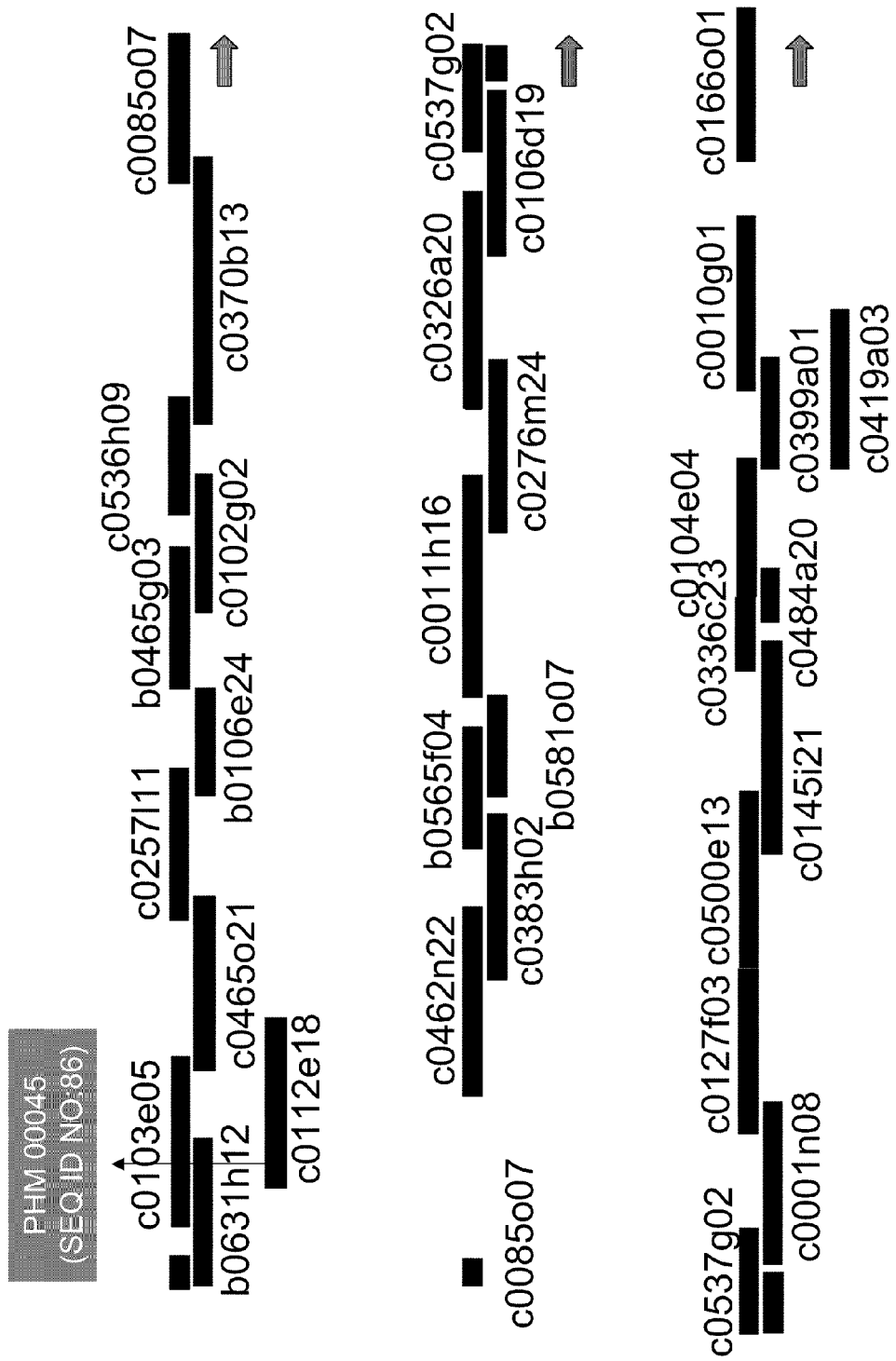
FIG. 4A GLS QTL Physical Map Location

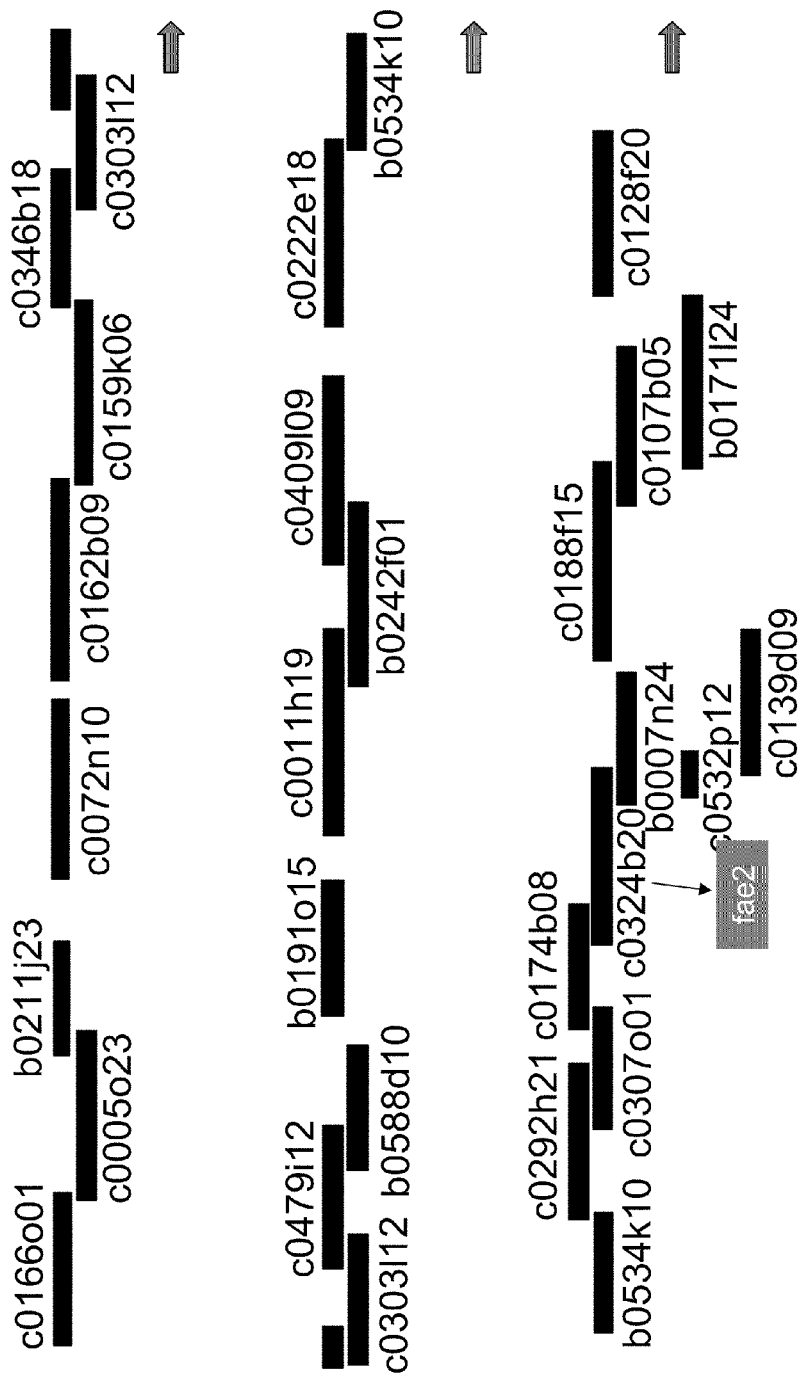
FIG. 4B GLS QTL Physical Map Location

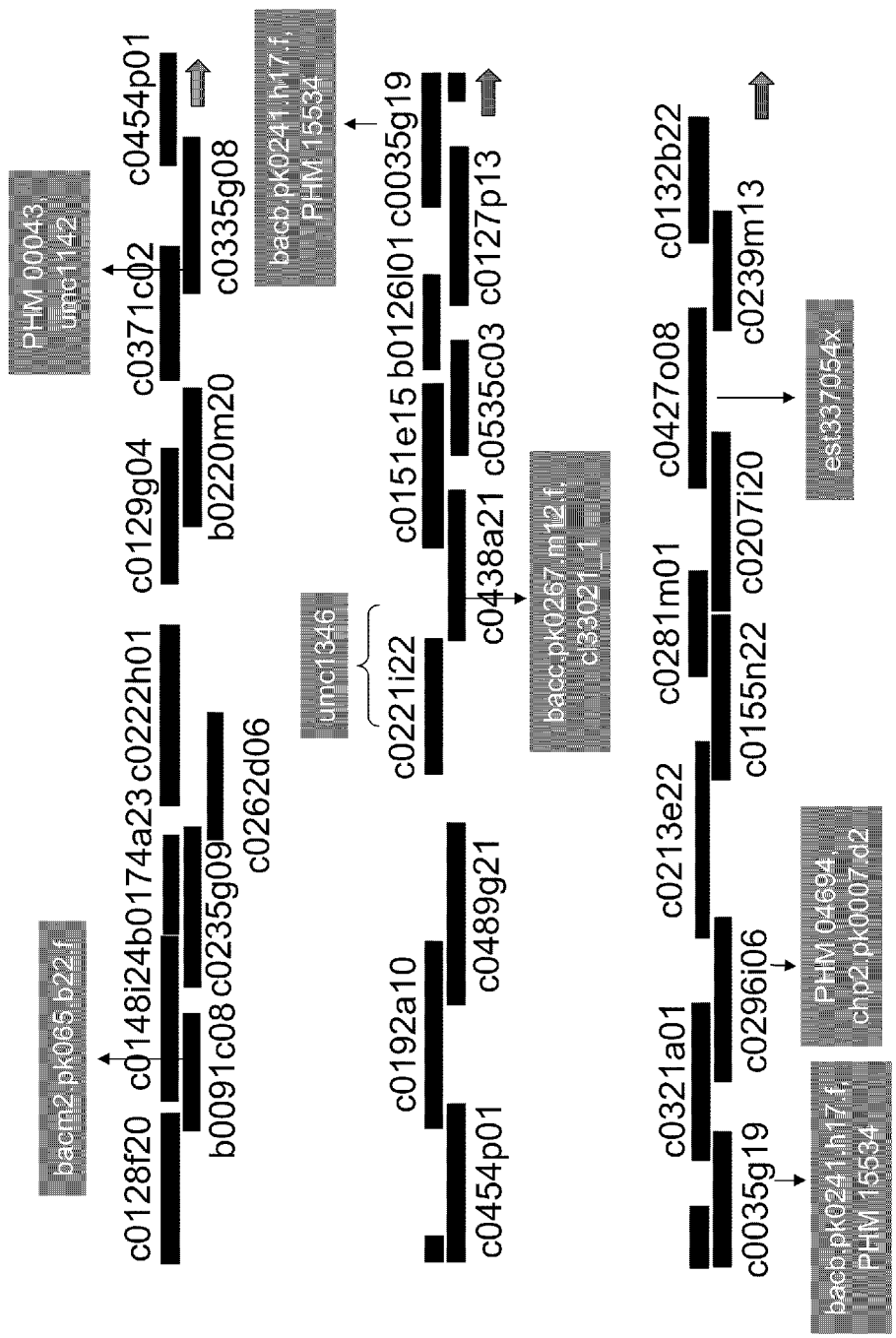
FIG. 4C GLS QTL Physical Map Location

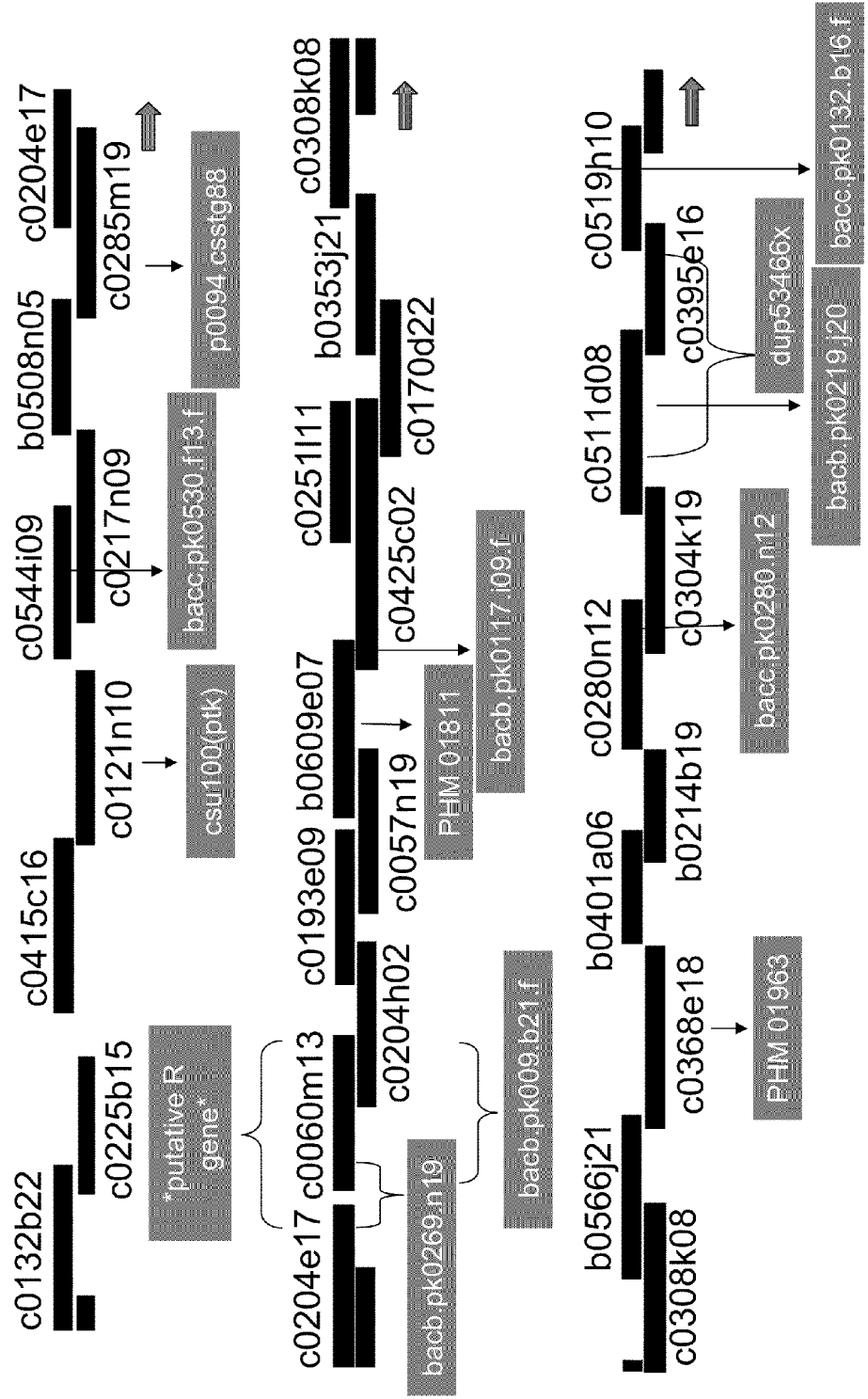
FIG. 4D GLS QTL Physical Map Location

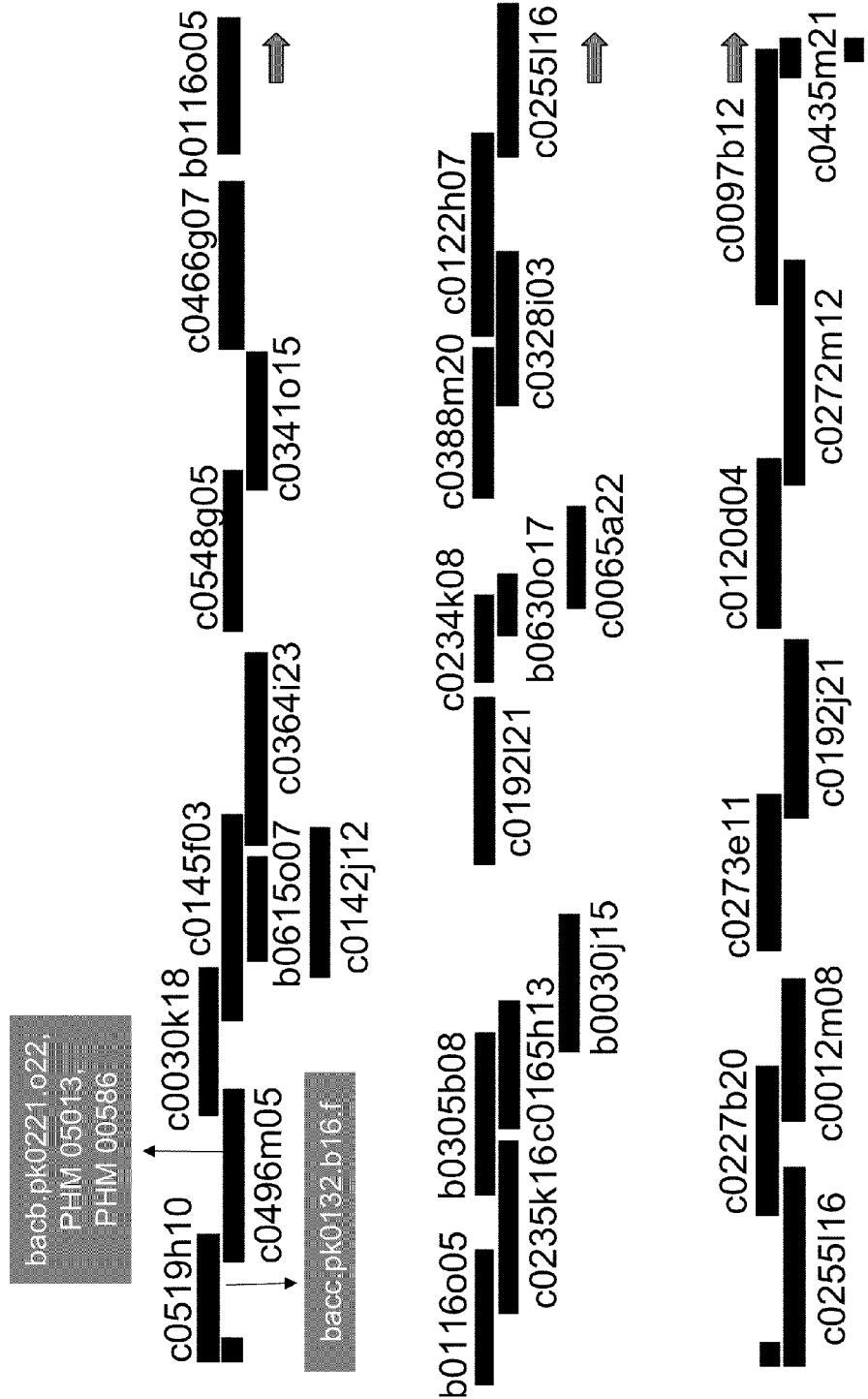
FIG. 4E GLS QTL Physical Map Location

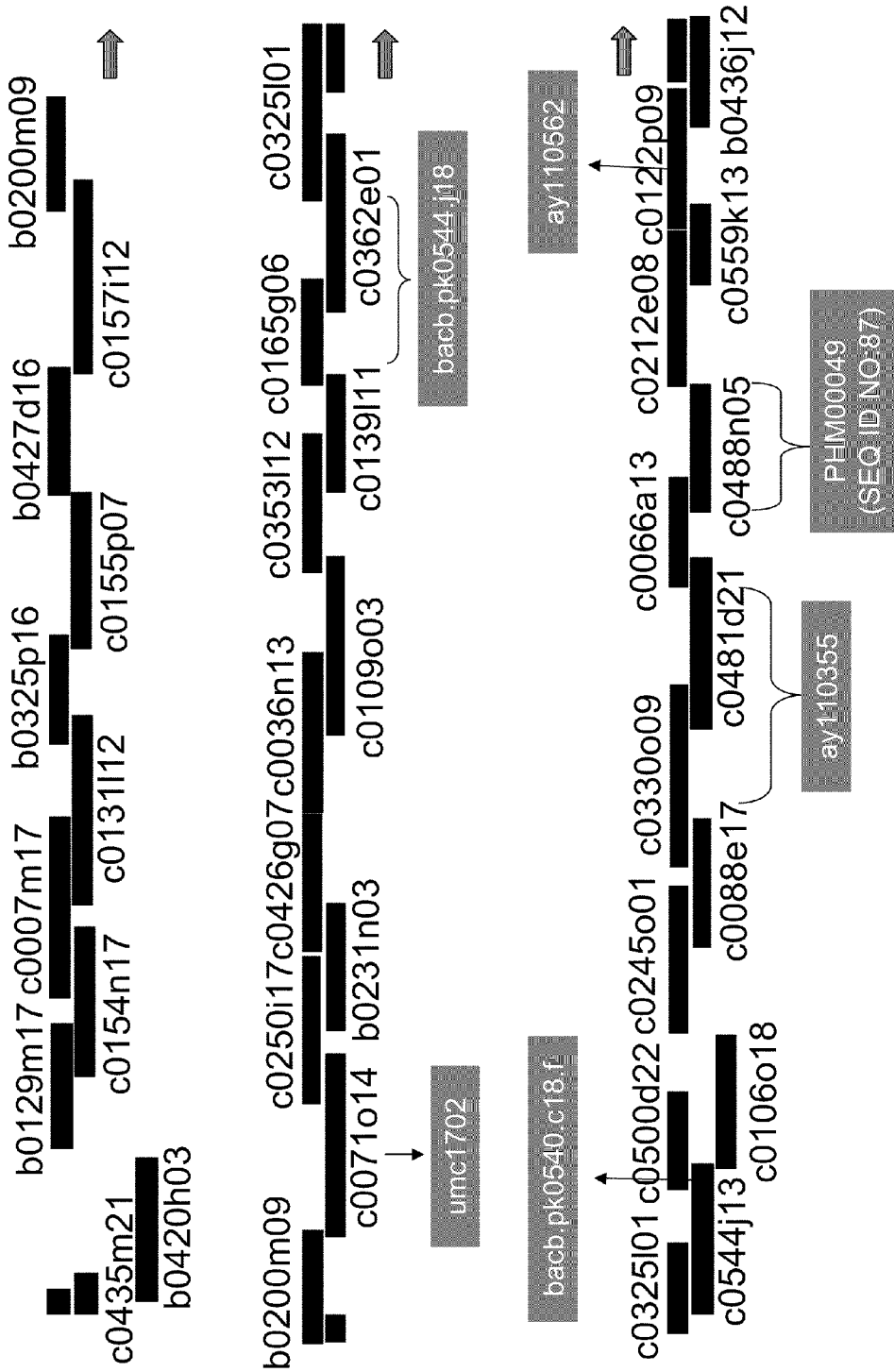

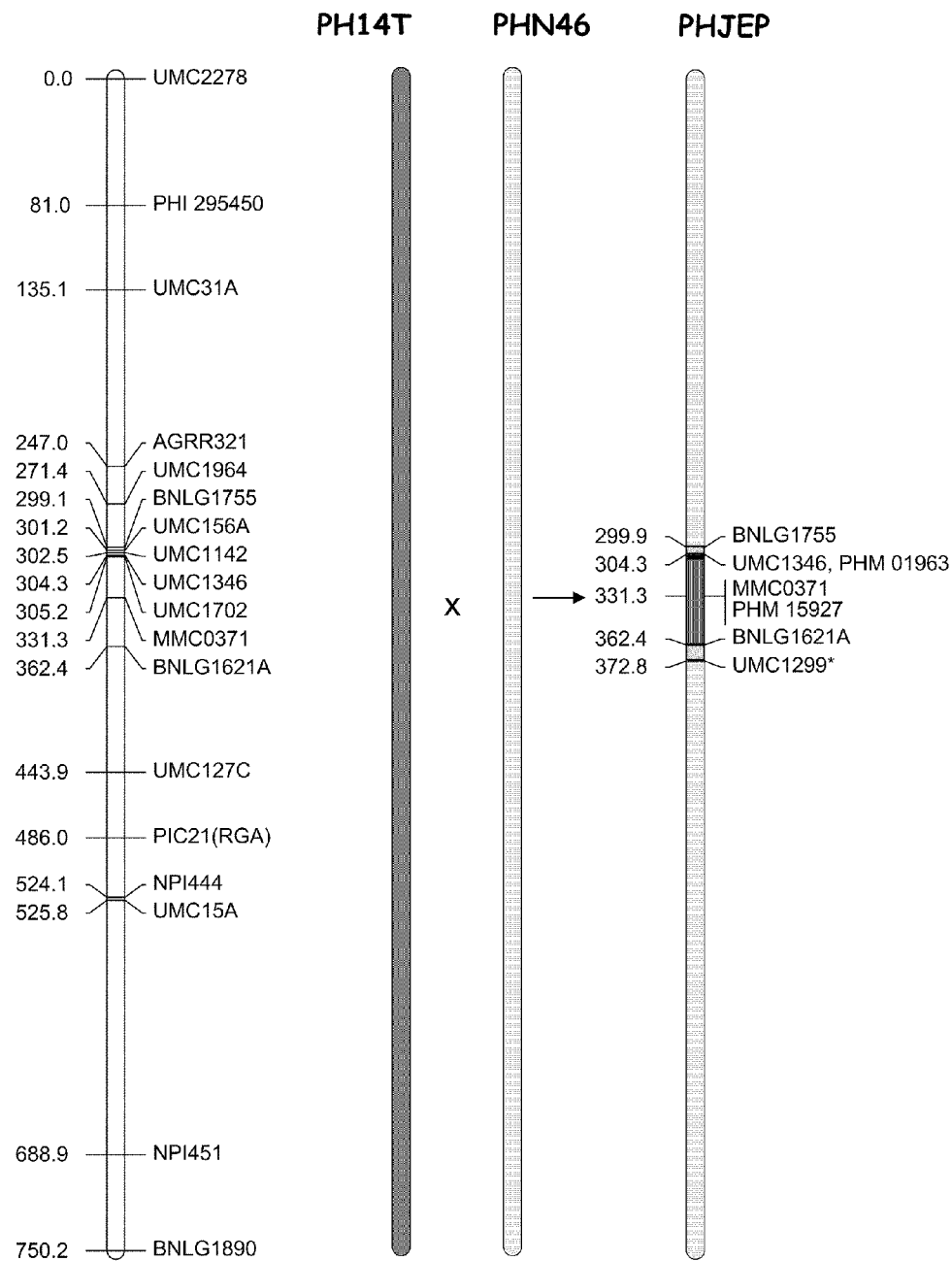
FIG. 5 Introgression of GLS QTL into PHN46

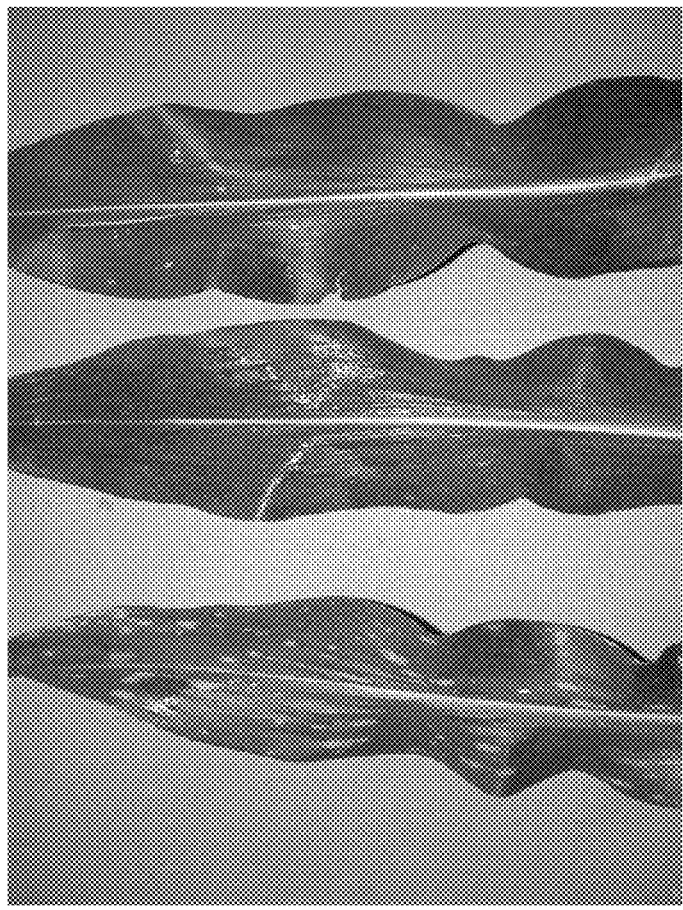
FIG. 6 Levels of Resistance to GLS

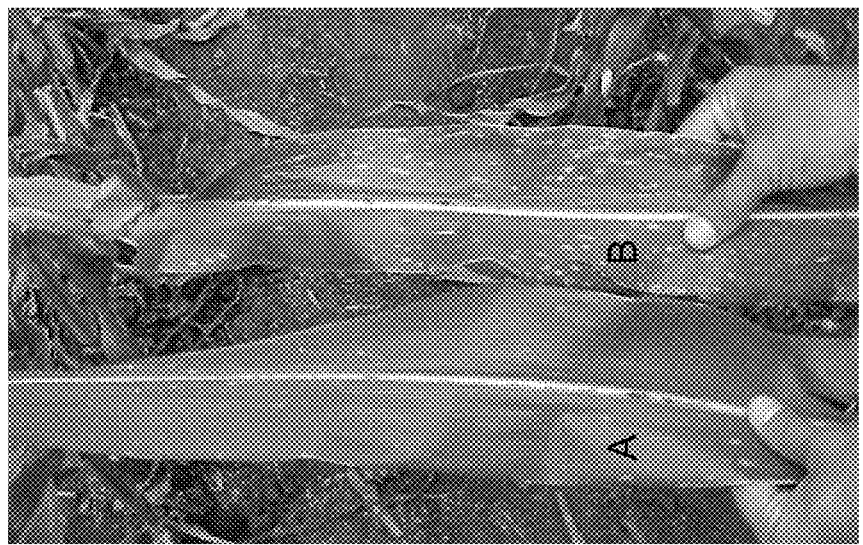
Fig. 7 Levels of Resistance to GLS: A) PHP38/PHJEP B) Pioneer Hybrid 3394

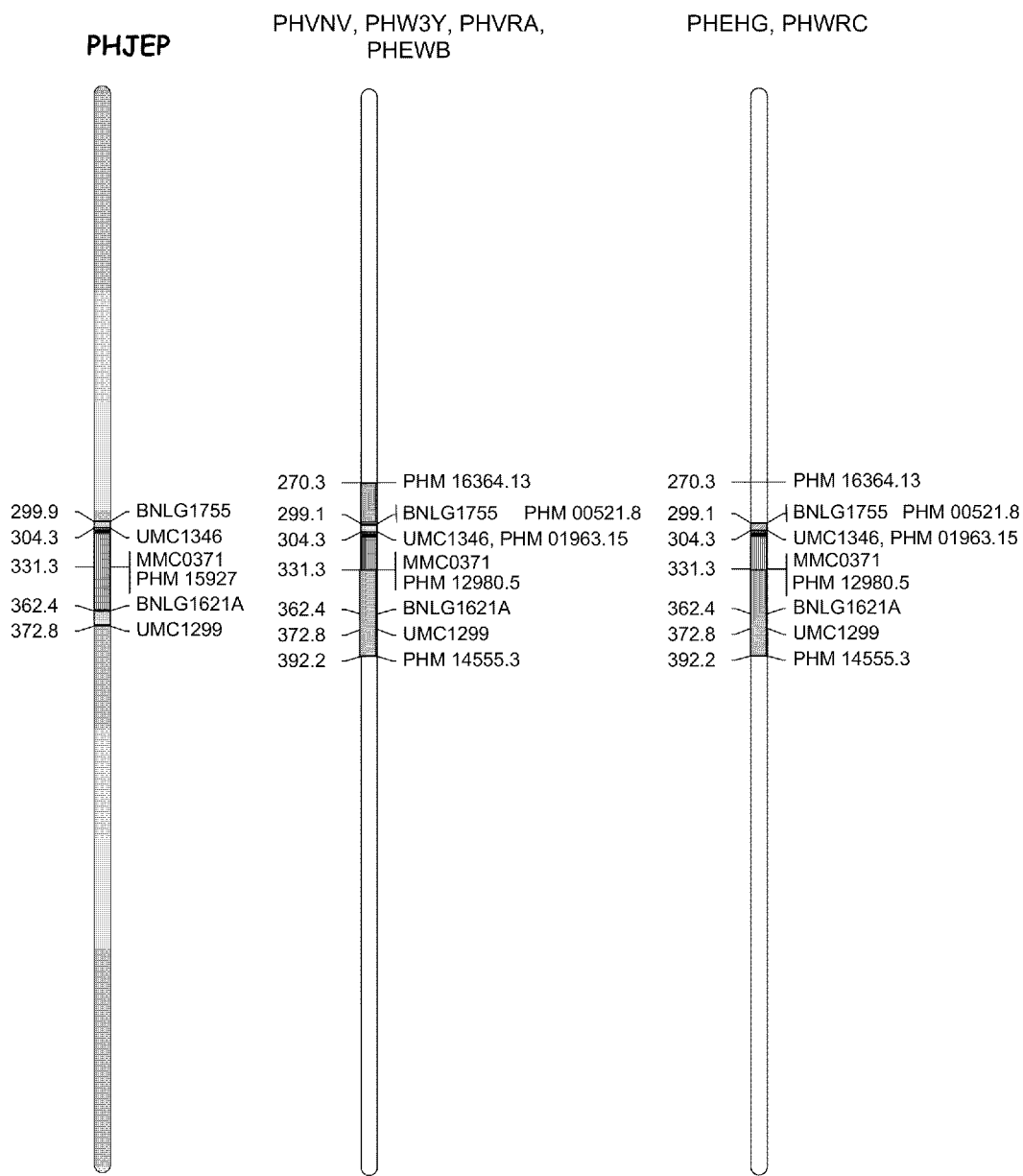
FIG. 8 Introgression of GLS QTL into Elite Materials

FIG. 9 SSR markers

| Marker Name | Left Primer Sequence | Right Primer Sequence | Repeat | Also Known As (AKA) |
|---|---|---|---|---|
| BNLG1755 | SEQ ID NO:86 | SEQ ID NO:87 | AG(27) | bmc1755, A5148A12, A5148A11, p-bnlg1755, bnlg1755 |
| UMC156A | SEQ ID NO:88 | SEQ ID NO:89 | | umc156, p-umc156 |
| UMC1142 | SEQ ID NO:90 | SEQ ID NO:91 | (TGGA)5 | umc1142, p-umc1142 |
| UMC1346 | SEQ ID NO:92 | SEQ ID NO:93 | (GCC)4 | umc1346, p-umc1346 |
| UMC1702 | SEQ ID NO:94 | SEQ ID NO:95 | (CAGCCT)4 | umc1702, p-umc1702 |
| MMC0371 | SEQ ID NO:96 | SEQ ID NO:97 | (GA)4N1(GA)23 (GGA)1(GAA)2 | mmc0371, p-mmc0371 |
| BNLG1621A | SEQ ID NO:98 | SEQ ID NO:99 | AG(18) | p-bnlg1621, A4750F07, A4750F06, bnlg1621, bmc1621 |
| UMC1299 | SEQ ID NO:100 | SEQ ID NO:101 | (AAG)5 | p-umc1299, umc1299 |

FIG. 10 SNP markers

| PHM Marker | Forward | Reverse | Probe 1 | Probe 2 | PHM reference | SNP |
|---|---|---|---|---|---|---|
| PHM 15534-13 | SEQ ID NO:51 | SEQ ID NO:52 | SEQ ID NO:53 | SEQ ID NO:54 | SEQ ID NO:55 | [at] (position 205) |
| PHM 04694-10 | SEQ ID NO:56 | SEQ ID NO:57 | SEQ ID NO:58 | SEQ ID NO:59 | SEQ ID NO:60 | [gt] (position 263) |
| PHM 01811-32 | SEQ ID NO:61 | SEQ ID NO:62 | SEQ ID NO:63 | SEQ ID NO:64 | SEQ ID NO:65 | [tc] (position 190) |
| PHM 01963-15 | SEQ ID NO:66 | SEQ ID NO:67 | SEQ ID NO:68 | SEQ ID NO:69 | SEQ ID NO:70 | [ct] (position 71) |
| PHM 01963-22 | SEQ ID NO:71 | SEQ ID NO:72 | SEQ ID NO:73 | SEQ ID NO:74 | SEQ ID NO:75 | [ct] (position 185) |
| PHM 05013-12 | SEQ ID NO:76 | SEQ ID NO:77 | SEQ ID NO:78 | SEQ ID NO:79 | SEQ ID NO:80 | [tc] (position 107) |
| PHM 00586-10 | SEQ ID NO:81 | SEQ ID NO:82 | SEQ ID NO:83 | SEQ ID NO:84 | SEQ ID NO:85 | [ct] (position 114) |

US 8,367,899 B2

SEQUENCE LISTING

<160> NUMBER OF SEQ ID NOS: 103

<210> SEQ ID NO 1
<211> LENGTH: 23
<212> TYPE: DNA
<213> ORGANISM: Artificial
<220> FEATURE:
<223> OTHER INFORMATION: BAC Primer

<400> SEQUENCE: 1
aatgatccat atacctccac tcc                                           23

<210> SEQ ID NO 2
<211> LENGTH: 20
<212> TYPE: DNA
<213> ORGANISM: Artificial
<220> FEATURE:
<223> OTHER INFORMATION: BAC Primer

<400> SEQUENCE: 2
ttcctggagg ttctgtttcg                                               20

<210> SEQ ID NO 3
<211> LENGTH: 19
<212> TYPE: DNA
<213> ORGANISM: Artificial
<220> FEATURE:
<223> OTHER INFORMATION: BAC Primer

<400> SEQUENCE: 3
gtgtggcttg gacatgacg                                                19

<210> SEQ ID NO 4
<211> LENGTH: 22
<212> TYPE: DNA
<213> ORGANISM: Artificial
<220> FEATURE:
<223> OTHER INFORMATION: BAC Primer

<400> SEQUENCE: 4
ggactctacg tgttctcttg gc                                            22

<210> SEQ ID NO 5
<211> LENGTH: 20
<212> TYPE: DNA
<213> ORGANISM: Artificial
<220> FEATURE:
<223> OTHER INFORMATION: BAC Primer

<400> SEQUENCE: 5
ggcaggtgtc acacaacaag                                               20

<210> SEQ ID NO 6
<211> LENGTH: 20
<212> TYPE: DNA
<213> ORGANISM: Artificial
<220> FEATURE:
<223> OTHER INFORMATION: BAC Primer

<400> SEQUENCE: 6
gcacaaacga gttcgtggat                                               20

<210> SEQ ID NO 7
<211> LENGTH: 20
<212> TYPE: DNA

```
<213> ORGANISM: Artificial
<220> FEATURE:
<223> OTHER INFORMATION: BAC Primer

<400> SEQUENCE: 7
tgcagctcat tttgttgtca                                        20

<210> SEQ ID NO 8
<211> LENGTH: 20
<212> TYPE: DNA
<213> ORGANISM: Artificial
<220> FEATURE:
<223> OTHER INFORMATION: BAC Primer

<400> SEQUENCE: 8
gagttgagct gcttccttgg                                        20

<210> SEQ ID NO 9
<211> LENGTH: 20
<212> TYPE: DNA
<213> ORGANISM: Artificial
<220> FEATURE:
<223> OTHER INFORMATION: BAC Primer

<400> SEQUENCE: 9
cctagggaca agaggtgtcg                                        20

<210> SEQ ID NO 10
<211> LENGTH: 20
<212> TYPE: DNA
<213> ORGANISM: Artificial
<220> FEATURE:
<223> OTHER INFORMATION: BAC Primer

<400> SEQUENCE: 10
actgttaccc gcacgttacc                                        20

<210> SEQ ID NO 11
<211> LENGTH: 20
<212> TYPE: DNA
<213> ORGANISM: Artificial
<220> FEATURE:
<223> OTHER INFORMATION: BAC Primer

<400> SEQUENCE: 11
tgtatcaagc cagcataggg                                        20

<210> SEQ ID NO 12
<211> LENGTH: 19
<212> TYPE: DNA
<213> ORGANISM: Artificial
<220> FEATURE:
<223> OTHER INFORMATION: BAC PrIMER

<400> SEQUENCE: 12
acagctgggt tgggatagg                                         19

<210> SEQ ID NO 13
<211> LENGTH: 20
<212> TYPE: DNA
<213> ORGANISM: Artificial
<220> FEATURE:
<223> OTHER INFORMATION: BAC Primer

<400> SEQUENCE: 13
cttcaagctc ctgagcaagc                                        20
```

```
<210> SEQ ID NO 14
<211> LENGTH: 20
<212> TYPE: DNA
<213> ORGANISM: Artificial
<220> FEATURE:
<223> OTHER INFORMATION: BAC Primer

<400> SEQUENCE: 14
gaacgagaca taggcgatgc                                              20

<210> SEQ ID NO 15
<211> LENGTH: 20
<212> TYPE: DNA
<213> ORGANISM: Artificial
<220> FEATURE:
<223> OTHER INFORMATION: BAC Primer

<400> SEQUENCE: 15
tactccagac cgctgaaacc                                              20

<210> SEQ ID NO 16
<211> LENGTH: 20
<212> TYPE: DNA
<213> ORGANISM: Artificial
<220> FEATURE:
<223> OTHER INFORMATION: BAC Primer

<400> SEQUENCE: 16
ggctcaaaga aaggtgatgc                                              20

<210> SEQ ID NO 17
<211> LENGTH: 20
<212> TYPE: DNA
<213> ORGANISM: Artificial
<220> FEATURE:
<223> OTHER INFORMATION: BAC Primer

<400> SEQUENCE: 17
agaaatggaa cgagcagagg                                              20

<210> SEQ ID NO 18
<211> LENGTH: 21
<212> TYPE: DNA
<213> ORGANISM: Artificial
<220> FEATURE:
<223> OTHER INFORMATION: BAC Primer

<400> SEQUENCE: 18
gtgactggtt gaagagcaag g                                            21

<210> SEQ ID NO 19
<211> LENGTH: 21
<212> TYPE: DNA
<213> ORGANISM: Artificial
<220> FEATURE:
<223> OTHER INFORMATION: BAC Primer

<400> SEQUENCE: 19
gaagtggtct cgatgttcag g                                            21

<210> SEQ ID NO 20
<211> LENGTH: 20
<212> TYPE: DNA
<213> ORGANISM: Artificial
<220> FEATURE:
<223> OTHER INFORMATION: BAC Primer
```

```
<400> SEQUENCE: 20
gctagccagc aatacaagcc                                          20

<210> SEQ ID NO 21
<211> LENGTH: 20
<212> TYPE: DNA
<213> ORGANISM: Artificial
<220> FEATURE:
<223> OTHER INFORMATION: BAC Primer

<400> SEQUENCE: 21
gaattcggca cgagtattgc                                          20

<210> SEQ ID NO 22
<211> LENGTH: 20
<212> TYPE: DNA
<213> ORGANISM: Artificial
<220> FEATURE:
<223> OTHER INFORMATION: BAC Primer

<400> SEQUENCE: 22
gaatcgaacg ccgtagtagg                                          20

<210> SEQ ID NO 23
<211> LENGTH: 20
<212> TYPE: DNA
<213> ORGANISM: Artificial
<220> FEATURE:
<223> OTHER INFORMATION: BAC Primer

<400> SEQUENCE: 23
gcagccaaat tgtttgaagg                                          20

<210> SEQ ID NO 24
<211> LENGTH: 20
<212> TYPE: DNA
<213> ORGANISM: Artificial
<220> FEATURE:
<223> OTHER INFORMATION: BAC Primer

<400> SEQUENCE: 24
gtaggctcgt caactttggg                                          20

<210> SEQ ID NO 25
<211> LENGTH: 20
<212> TYPE: DNA
<213> ORGANISM: Artificial
<220> FEATURE:
<223> OTHER INFORMATION: BAC Primer

<400> SEQUENCE: 25
atttgcatat gcctccatgc                                          20

<210> SEQ ID NO 26
<211> LENGTH: 20
<212> TYPE: DNA
<213> ORGANISM: Artificial
<220> FEATURE:
<223> OTHER INFORMATION: BAC Primer

<400> SEQUENCE: 26
aagattccgg tgttgaatgc                                          20

<210> SEQ ID NO 27
<211> LENGTH: 20
<212> TYPE: DNA
```

-continued

<213> ORGANISM: Artificial
<220> FEATURE:
<223> OTHER INFORMATION: BAC Primer

<400> SEQUENCE: 27
gcccccttct tcttcaactc                                               20

<210> SEQ ID NO 28
<211> LENGTH: 20
<212> TYPE: DNA
<213> ORGANISM: Artificial
<220> FEATURE:
<223> OTHER INFORMATION: BAC Primer

<400> SEQUENCE: 28
gcttttattg gtgcggtcat                                               20

<210> SEQ ID NO 29
<211> LENGTH: 20
<212> TYPE: DNA
<213> ORGANISM: Artificial
<220> FEATURE:
<223> OTHER INFORMATION: BAC Primer

<400> SEQUENCE: 29
gacaccgaac catagcttcc                                               20

<210> SEQ ID NO 30
<211> LENGTH: 22
<212> TYPE: DNA
<213> ORGANISM: Artificial
<220> FEATURE:
<223> OTHER INFORMATION: BAC Primer

<400> SEQUENCE: 30
cttgaacttg ctcaatcttt cc                                            22

<210> SEQ ID NO 31
<211> LENGTH: 19
<212> TYPE: DNA
<213> ORGANISM: Artificial
<220> FEATURE:
<223> OTHER INFORMATION: BAC Primer

<400> SEQUENCE: 31
ccggtgagtt tgttgttgg                                                19

<210> SEQ ID NO 32
<211> LENGTH: 20
<212> TYPE: DNA
<213> ORGANISM: Artificial
<220> FEATURE:
<223> OTHER INFORMATION: BAC Primer

<400> SEQUENCE: 32
ggaaggtttc gtcaatcagc                                               20

<210> SEQ ID NO 33
<211> LENGTH: 20
<212> TYPE: DNA
<213> ORGANISM: Artificial
<220> FEATURE:
<223> OTHER INFORMATION: BAC Primer

<400> SEQUENCE: 33
accatacctg agtgggaacg                                               20

```
<210> SEQ ID NO 34
<211> LENGTH: 20
<212> TYPE: DNA
<213> ORGANISM: Artificial
<220> FEATURE:
<223> OTHER INFORMATION: BAC Primer

<400> SEQUENCE: 34
aagccatcca gaccttctcc                                              20

<210> SEQ ID NO 35
<211> LENGTH: 20
<212> TYPE: DNA
<213> ORGANISM: Artificial
<220> FEATURE:
<223> OTHER INFORMATION: BAC Primer

<400> SEQUENCE: 35
catcccacca catcgctatt                                              20

<210> SEQ ID NO 36
<211> LENGTH: 20
<212> TYPE: DNA
<213> ORGANISM: Artificial
<220> FEATURE:
<223> OTHER INFORMATION: BAC Primer

<400> SEQUENCE: 36
tgtcccatac ccgtacccta                                              20

<210> SEQ ID NO 37
<211> LENGTH: 21
<212> TYPE: DNA
<213> ORGANISM: Artificial
<220> FEATURE:
<223> OTHER INFORMATION: BAC Primer

<400> SEQUENCE: 37
tggaaatttg gtgttcattg c                                            21

<210> SEQ ID NO 38
<211> LENGTH: 20
<212> TYPE: DNA
<213> ORGANISM: Artificial
<220> FEATURE:
<223> OTHER INFORMATION: BAC Primer

<400> SEQUENCE: 38
agtggatgcc ttctgagtgc                                              20

<210> SEQ ID NO 39
<211> LENGTH: 20
<212> TYPE: DNA
<213> ORGANISM: Artificial
<220> FEATURE:
<223> OTHER INFORMATION: BAC Primer

<400> SEQUENCE: 39
tcttgagtgt tgctcccaaa                                              20

<210> SEQ ID NO 40
<211> LENGTH: 20
<212> TYPE: DNA
<213> ORGANISM: Artificial
<220> FEATURE:
<223> OTHER INFORMATION: BAC Primer
```

<400> SEQUENCE: 40
ttccttttgt ggctttgacc                                          20

<210> SEQ ID NO 41
<211> LENGTH: 20
<212> TYPE: DNA
<213> ORGANISM: Artificial
<220> FEATURE:
<223> OTHER INFORMATION: BAC Primer

<400> SEQUENCE: 41
gagattgcat gcccaaaaat                                          20

<210> SEQ ID NO 42
<211> LENGTH: 20
<212> TYPE: DNA
<213> ORGANISM: Artificial
<220> FEATURE:
<223> OTHER INFORMATION: BAC Primer

<400> SEQUENCE: 42
cggatgcaca aactgcttta                                          20

<210> SEQ ID NO 43
<211> LENGTH: 20
<212> TYPE: DNA
<213> ORGANISM: Artificial
<220> FEATURE:
<223> OTHER INFORMATION: BAC Primer

<400> SEQUENCE: 43
tcgtgtagct cctgtcaacg                                          20

<210> SEQ ID NO 44
<211> LENGTH: 20
<212> TYPE: DNA
<213> ORGANISM: Artificial
<220> FEATURE:
<223> OTHER INFORMATION: BAC Primer

<400> SEQUENCE: 44
gtgaacgcgt tttgcaacta                                          20

<210> SEQ ID NO 45
<211> LENGTH: 20
<212> TYPE: DNA
<213> ORGANISM: Artificial
<220> FEATURE:
<223> OTHER INFORMATION: BAC Primer

<400> SEQUENCE: 45
cctggtgaat gaatggttcc                                          20

<210> SEQ ID NO 46
<211> LENGTH: 21
<212> TYPE: DNA
<213> ORGANISM: Artificial
<220> FEATURE:
<223> OTHER INFORMATION: BAC Primer

<400> SEQUENCE: 46
tctacacaat gccaagtcag c                                        21

<210> SEQ ID NO 47
<211> LENGTH: 20
<212> TYPE: DNA

```
<213> ORGANISM: Artificial
<220> FEATURE:
<223> OTHER INFORMATION: BAC Primer

<400> SEQUENCE: 47
tcccgtgttt cttgtcgtgt                                                    20

<210> SEQ ID NO 48
<211> LENGTH: 22
<212> TYPE: DNA
<213> ORGANISM: Artificial
<220> FEATURE:
<223> OTHER INFORMATION: BAC Primer

<400> SEQUENCE: 48
agtcatattt acgctaggaa cg                                                 22

<210> SEQ ID NO 49
<211> LENGTH: 4156
<212> TYPE: DNA
<213> ORGANISM: Zea mays

<400> SEQUENCE: 49
cgcgctaata gacgaacggg atgaaagcag aaaagtgacg gcaagtaaat gacgagagtt        60
tgacggactc acggtcttct cttcaccggc ggtcaagcta agcctagtgc tgttctgtgg       120
atgtaacggt gctgtaaaag ggtttataaa ccacatagga ggtcagccag ctgagtatcc       180
agtttaaagt tcagagttca atctcacagc accaagcaaa aaggaagcag attaagggca       240
gccgagcgag cagaggtacc tcgttctctc tttctccttc cgtacataat tatccaattt       300
agcttgtact tgttaagaat tcgtttagta agtttgtagt aagcttggtc actccttgaa       360
ctaagcgtag tactttctcc gtaatacgcc gccaagagat cattctttat tttttgcagg       420
ttgtcaatta cgtgccttaa tgagtcactg gaagcagccg tcgaaactcg ccatgcttgt       480
agtactgctg ctgctgctat gtcatgcagt ggacagagtc cattgctcga cgcatcataa       540
caacagccaa gattttcatt cgctgcttga gttccacaag ggcatcacca gtgatccgca       600
cggagccttg agcaattgga acccccagcat acacttctgc cattggcatg gtgtgaactg       660
cagttccact cgaccatatc gagtcacgga gctcaatctc aacggccaaa gcttggctgg       720
ccaaatcagc tcctctcttg gaaacctgac cttccttcag acccttgatc ttagcaacaa       780
tagcttcatt ggcccccctac ctcttcttaa caagctccga aacctggacg tacttttttt       840
tctgggaagc aacctttggg aggatgttat tcctgattgg cttacaaact gttctaactt       900
agtccaacta gatctctctg aaaacaatct caccggtcat attccttcaa acatagacat       960
tctaaaaaag ctagaatata taggccttta ctataataat ctcaccggtg tcatcccacc      1020
aaccttggga acatctcca cactagatgt agttgatctt tcaatgaatc aactaagtgg      1080
aagcattcct gatgatgttt ggaaaatatc gaacataaca cagttatttc tacaacaaaa      1140
taatctatca ggcggaatcc tagatactct ctctaaatta tcttctcttg tgatattaaa      1200
cttgcacacc aatatgttgg gaggcacatt gccatcaaac attggtgatg tgctccctaa      1260
tctgcaagaa ctatacttag gaaagaataa ttttgtgggt acaattccaa attccctagg      1320
taatccttcg agtcttaaaa tcatagatct atcaataaac tattttaggg gcaaaattcc      1380
gaactctttt ggaaatcttt cacatttgca gtctctaaac cttgaggtaa acatgcttgg      1440
atcaagggat agtgaaggct tgcaattctt tgatgccctc gcaaattgta gatctctcgt      1500
tacactttca gtgtccaata atcagctaca tggtcctata ccaaactcga ttgctaatct      1560
```

```
gtccactagt cttggacaac tagtgatggg ttggaacagc ctatcaggaa caattccccc      1620
aaccattgga aaacttagtg gcttatatag attatcacta caaaacaata atcttacagg      1680
taccattgag gaatggatcg gaaagatgac aaatctacaa tttttaacac tacagtcaaa      1740
caacttcata gggaaaattc caccttcaat tggcaatctt acacagttga tagatatctt      1800
ctctgtagcc aaaaacaatt tatctggttt tgtaccatct aacttctgga atcttaaaat      1860
atcgaagttg gaccttagcc ataacaattt ccaaggagc atacctgttc aatttagtaa       1920
cttagaactc atctggctaa atctttcatc aaacaaattt agtggtgaaa ttcctggaac      1980
tttaggacaa cttgaacaaa tacagaccat tcaaatggac caaaacattc ttactggaaa      2040
cattccgccc atatttagtc gactatatag cttgaacttg ctcaatcttt cccataacaa      2100
tttatctggc cccatgccaa ctttctaag tggtctaaat cttagtaaac tagatctatc       2160
ctacaacaat tttcaaggac aaataccaag aactggtgta ttcaataatc ccacaattgt      2220
ttcactagat ggcaatccag aattgtgtgg aggagccatg gatttgcata tgcctccgtg      2280
ccatgatact tcaaaaagag taggtagatc aaacttattg atcaaaatat tgatcccaat      2340
ttttgggttc atgtcactcg tattgctggc ctactttta ctcctagaga agaggacgtc        2400
aagaagagaa tctagattag agctatcata ttgtgagcat tttgagacag ttacttataa      2460
cgacttagct caagcaacac gggacttctc agaatccaac ctaattggga gaggaagcta      2520
tggttcggtg taccgaggga agctaaagga aagcaaaatc gaagtggcag taaaggtttt      2580
tgaccttaag atgagaggag cagaaagaag cttcttgtca gaatgtgaag cattgagaag      2640
cattcaacac cgaaatcttc ttcccatcat aactgcttgc tcaacagtag ataatgtagg      2700
aaatgttttc aaagctttaa tttatgagtt catgcctaat gggagcctgg acgcatggct      2760
acatcacaaa ggagatgagg agaccgcaaa atgtcttggc ttgactcaga gaataagcat      2820
agctatcaat atagctgacg cattggatta tttgcaccat gattgtggac gaccaactgt      2880
ccattgcgac ttgaaaccca gcaatatcct tctagatgat gacatgaatg ctcttttggg      2940
agattttgga atttcgcgct tctatcatga ttctcagtca aaatgggcag gttcaattag      3000
ttcaattggt gtaaagggaa caattggata tattcctcca ggtacctata gttacttcag      3060
ttattctttg ttgttcataa ttttctagg tagaaaataa cttaaaaccc aacaattaat      3120
ttgtgtgcac atttccaat tcagagtacg gaggaggtgg ccatgcatca acgtctgggg       3180
atgtttatag ttttgggata gtgttgctgg agattttgac gagcaaaagg ccaacagatc      3240
ctctgttcaa ggatggccag gacatcatca gctttgtgga gaataacttt ccggatcaag      3300
tctttcaagt cattgactct cacctcctag atgaatgcag gaactcaatt caaggaaata      3360
atttggtacc agaaaatgag atctaccaat gcttggttga ccttctgcaa ttagcacttt      3420
cgtgccttcg ttcattacca tctgaacgat caaacatgaa gcaagtagcc agcagaatgc      3480
atgcaatcca aacatcatat cttcggtgga agaagaagta ataagaggaa gggtgttccc      3540
tgaattgtaa aataacatat atacttagac atccactcgc atgtattatt gattatcatc      3600
tagaaaatac aagaataaaa cccttgcaat agaaatatgc taaacatcgt gataatatca      3660
aaatatggaa gaaatgtagg attcccaatt tgttatggag acatagaaat cataaatttg      3720
cagtggagcg agtattcttt gtaactgtgg ccgattttct agatgatgtg gtagtttaaa      3780
gttcccaagc aagctacaat actacatgtt attgatgttg taagttatta gtagtcataa      3840
taaaaatgac aaagataatg gccaaattag tgggatagta ttgcatctaa ttggtggaag      3900
tttatctatt ctacaatata tcgatgatac tattattttt atagatcatg acctagaaaa      3960
```

-continued

```
gggttgagaa ttgatggtat ttctttatgt gttcttggaa ccgtcaggtc acaaaaaatt    4020
aaaagggtca tgatatccat gaggatgagt aaattgagct aatttaaaaa aaattataac    4080
aattaaaact tattgcatcc tacttcactc cttgttttag agtgttttgc accctaggca    4140
taaggaaaat agatcg                                                    4156
```

<210> SEQ ID NO 50
<211> LENGTH: 886
<212> TYPE: PRT
<213> ORGANISM: Zea mays

<400> SEQUENCE: 50

```
Met Ser His Trp Lys Gln Pro Ser Lys Leu Ala Met Leu Val Val Leu
1               5                   10                  15

Leu Leu Leu Cys His Ala Val Asp Arg Val His Cys Ser Thr His
            20                  25                  30

His Asn Asn Ser Gln Asp Phe His Ser Leu Leu Glu Phe His Lys Gly
        35                  40                  45

Ile Thr Ser Asp Pro His Gly Ala Leu Ser Asn Trp Asn Pro Ser Ile
    50                  55                  60

His Phe Cys His Trp His Gly Val Asn Cys Ser Ser Thr Arg Pro Tyr
65                  70                  75                  80

Arg Val Thr Glu Leu Asn Leu Asn Gly Gln Ser Leu Ala Gly Gln Ile
                85                  90                  95

Ser Ser Ser Leu Gly Asn Leu Thr Phe Leu Gln Thr Leu Asp Leu Ser
            100                 105                 110

Asn Asn Ser Phe Ile Gly Pro Leu Pro Leu Leu Asn Lys Leu Arg Asn
        115                 120                 125

Leu Asp Val Leu Phe Phe Leu Gly Ser Asn Leu Leu Glu Asp Val Ile
    130                 135                 140

Pro Asp Trp Leu Thr Asn Cys Ser Asn Leu Val Gln Leu Asp Leu Ser
145                 150                 155                 160

Glu Asn Asn Leu Thr Gly His Ile Pro Ser Asn Ile Asp Ile Leu Lys
                165                 170                 175

Lys Leu Glu Tyr Ile Gly Leu Tyr Tyr Asn Asn Leu Thr Gly Val Ile
            180                 185                 190

Pro Pro Thr Leu Gly Asn Ile Ser Thr Leu Asp Val Val Asp Leu Ser
        195                 200                 205

Met Asn Gln Leu Ser Gly Ser Ile Pro Asp Asp Val Trp Lys Ile Ser
    210                 215                 220

Asn Ile Thr Gln Leu Phe Leu Gln Gln Asn Asn Leu Ser Gly Gly Ile
225                 230                 235                 240

Leu Asp Thr Leu Ser Lys Leu Ser Ser Leu Val Ile Leu Asn Leu His
                245                 250                 255

Thr Asn Met Leu Gly Gly Thr Leu Pro Ser Asn Ile Gly Asp Val Leu
            260                 265                 270

Pro Asn Leu Gln Glu Leu Tyr Leu Gly Lys Asn Asn Phe Val Gly Thr
        275                 280                 285

Ile Pro Asn Ser Leu Gly Asn Pro Ser Ser Leu Lys Ile Ile Asp Leu
    290                 295                 300

Ser Ile Asn Tyr Phe Arg Gly Lys Ile Pro Asn Ser Phe Gly Asn Leu
305                 310                 315                 320

Ser His Leu Gln Ser Leu Asn Leu Glu Val Asn Met Leu Gly Ser Arg
                325                 330                 335

Asp Ser Glu Gly Leu Gln Phe Phe Asp Ala Leu Ala Asn Cys Arg Ser
```

```
                    340             345             350
Leu Val Thr Leu Ser Val Ser Asn Asn Gln Leu His Gly Pro Ile Pro
            355                 360                 365

Asn Ser Ile Ala Asn Leu Ser Thr Ser Leu Gly Gln Leu Val Met Gly
            370                 375             380

Trp Asn Ser Leu Ser Gly Thr Ile Pro Pro Thr Ile Gly Lys Leu Ser
385                 390                 395                 400

Gly Leu Tyr Arg Leu Ser Leu Gln Asn Asn Asn Leu Thr Gly Thr Ile
                405                 410                 415

Glu Glu Trp Ile Gly Lys Met Thr Asn Leu Gln Phe Leu Thr Leu Gln
            420                 425                 430

Ser Asn Asn Phe Ile Gly Lys Ile Pro Pro Ser Ile Gly Asn Leu Thr
            435                 440                 445

Gln Leu Ile Asp Ile Phe Ser Val Ala Lys Asn Asn Leu Ser Gly Phe
        450                 455                 460

Val Pro Ser Asn Phe Trp Asn Leu Lys Ile Ser Lys Leu Asp Leu Ser
465                 470                 475                 480

His Asn Asn Phe Gln Gly Ser Ile Pro Val Gln Phe Ser Asn Leu Glu
                485                 490                 495

Leu Ile Trp Leu Asn Leu Ser Ser Asn Lys Phe Ser Gly Glu Ile Pro
            500                 505                 510

Gly Thr Leu Gly Gln Leu Glu Ile Gln Thr Ile Gln Met Asp Gln
            515                 520                 525

Asn Ile Leu Thr Gly Asn Ile Pro Pro Ile Phe Ser Arg Leu Tyr Ser
            530                 535                 540

Leu Asn Leu Leu Asn Leu Ser His Asn Asn Leu Ser Gly Pro Met Pro
545                 550                 555                 560

Thr Phe Leu Ser Gly Leu Asn Leu Ser Lys Leu Asp Leu Ser Tyr Asn
                565                 570                 575

Asn Phe Gln Gly Gln Ile Pro Arg Thr Gly Val Phe Asn Asn Pro Thr
            580                 585                 590

Ile Val Ser Leu Asp Gly Asn Pro Glu Leu Cys Gly Gly Ala Met Asp
            595                 600                 605

Leu His Met Pro Pro Cys His Asp Thr Ser Lys Arg Val Gly Arg Ser
        610                 615                 620

Asn Leu Leu Ile Lys Ile Leu Ile Pro Ile Phe Gly Phe Met Ser Leu
625                 630                 635                 640

Val Leu Leu Ala Tyr Phe Leu Leu Glu Lys Arg Thr Ser Arg Arg
                645                 650                 655

Glu Ser Arg Leu Glu Leu Ser Tyr Cys Glu His Phe Glu Thr Val Thr
            660                 665                 670

Tyr Asn Asp Leu Ala Gln Ala Thr Arg Asp Phe Ser Glu Ser Asn Leu
        675                 680                 685

Ile Gly Arg Gly Ser Tyr Gly Ser Val Tyr Arg Gly Lys Leu Lys Glu
            690                 695                 700

Ser Lys Ile Glu Val Ala Val Lys Val Phe Asp Leu Lys Met Arg Gly
705                 710                 715                 720

Ala Glu Arg Ser Phe Leu Ser Glu Cys Glu Ala Leu Arg Ser Ile Gln
                725                 730                 735

His Arg Asn Leu Leu Pro Ile Ile Thr Ala Cys Ser Thr Val Asp Asn
            740                 745                 750

Val Gly Asn Val Phe Lys Ala Leu Ile Tyr Glu Phe Met Pro Asn Gly
            755                 760                 765
```

```
Ser Leu Asp Ala Trp Leu His His Lys Gly Asp Glu Glu Thr Ala Lys
        770                 775                 780

Cys Leu Gly Leu Thr Gln Arg Ile Ser Ile Ala Ile Asn Ile Ala Asp
785                 790                 795                 800

Ala Leu Asp Tyr Leu His His Asp Cys Gly Arg Pro Thr Val His Cys
                805                 810                 815

Asp Leu Lys Pro Ser Asn Ile Leu Leu Asp Asp Met Asn Ala Leu
                820                 825                 830

Leu Gly Asp Phe Gly Ile Ser Arg Phe Tyr His Asp Ser Gln Ser Lys
                835                 840                 845

Trp Ala Gly Ser Ile Ser Ser Ile Gly Val Lys Gly Thr Ile Gly Tyr
        850                 855                 860

Ile Pro Pro Gly Thr Tyr Ser Tyr Phe Ser Tyr Ser Leu Leu Phe Ile
865                 870                 875                 880

Ile Phe Leu Gly Arg Lys
                885

<210> SEQ ID NO 51
<211> LENGTH: 22
<212> TYPE: DNA
<213> ORGANISM: Artificial
<220> FEATURE:
<223> OTHER INFORMATION: Primer

<400> SEQUENCE: 51
ttcattgatg gcctagccga ca                                           22

<210> SEQ ID NO 52
<211> LENGTH: 29
<212> TYPE: DNA
<213> ORGANISM: Artificial
<220> FEATURE:
<223> OTHER INFORMATION: Primer

<400> SEQUENCE: 52 acaactttttg ctttatccac tgtcgatca                                   29

<210> SEQ ID NO 53
<211> LENGTH: 22
<212> TYPE: DNA
<213> ORGANISM: Artificial
<220> FEATURE:
<223> OTHER INFORMATION: Probe

<400> SEQUENCE: 53
agatgttagt tttgaacaca aa                                           22

<210> SEQ ID NO 54
<211> LENGTH: 22
<212> TYPE: DNA
<213> ORGANISM: Artificial
<220> FEATURE:
<223> OTHER INFORMATION: Probe

<400> SEQUENCE: 54
tgatgttagt tttgaacaca aa                                           22

<210> SEQ ID NO 55
<211> LENGTH: 363
<212> TYPE: DNA
<213> ORGANISM: Artificial
<220> FEATURE:
<223> OTHER INFORMATION: SNP consensus
<220> FEATURE:
```

```
<221> NAME/KEY: misc_feature
<222> LOCATION: (349)..(349)
<223> OTHER INFORMATION: n is a, g, c, or t

<400> SEQUENCE: 55
aatggcagga atctgtgggc tttatgaaag gaaaattagg gatatcaacc caatgatccc      60
aaacataact tatgacatca gcgacctcta taacttcatt gatggcctag ccgacattag     120
tgcgctggtg taagtacaac ttttttaaga ttttcaaagt tgcatgaagt atatttatgc     180
atgtttgtgt tcaaaactaa catcwtaata attgtgctcc yctttccata tgcagttatg     240
atcactcgat tcaggcattc ctgccatatg atcgacagtg gataaagcaa aagttgtttc     300
aacacctgaa gaaattggct cagcggtagc acaactgttg tttsttctng atgcctttta     360
tcc                                                                   363

<210> SEQ ID NO 56
<211> LENGTH: 30
<212> TYPE: DNA
<213> ORGANISM: Artificial
<220> FEATURE:
<223> OTHER INFORMATION: Primer

<400> SEQUENCE: 56
catgaaacat tcgacatttc gtttacagga                                       30

<210> SEQ ID NO 57
<211> LENGTH: 20
<212> TYPE: DNA
<213> ORGANISM: Artificial
<220> FEATURE:
<223> OTHER INFORMATION: Primer

<400> SEQUENCE: 57
gaggaatggc cgaccgaaga                                                  20

<210> SEQ ID NO 58
<211> LENGTH: 18
<212> TYPE: DNA
<213> ORGANISM: Artificial
<220> FEATURE:
<223> OTHER INFORMATION: Primer

<400> SEQUENCE: 58
tttgctacta catgcagc                                                    18

<210> SEQ ID NO 59
<211> LENGTH: 18
<212> TYPE: DNA
<213> ORGANISM: Artificial
<220> FEATURE:
<223> OTHER INFORMATION: Primer

<400> SEQUENCE: 59
gttgctacta catgcagc                                                    18

<210> SEQ ID NO 60
<211> LENGTH: 387
<212> TYPE: DNA
<213> ORGANISM: Artificial
<220> FEATURE:
<223> OTHER INFORMATION: SNP consensus
<220> FEATURE:
<221> NAME/KEY: misc_feature
<222> LOCATION: (132)..(140)
<223> OTHER INFORMATION: n is a, g, c, or t
<220> FEATURE:
```

```
<221> NAME/KEY: misc_feature
<222> LOCATION: (332)..(332)
<223> OTHER INFORMATION: n is a, g, c, or t
<220> FEATURE:
<221> NAME/KEY: misc_feature
<222> LOCATION: (342)..(342)
<223> OTHER INFORMATION: n is a, g, c, or t
<220> FEATURE:
<221> NAME/KEY: misc_feature
<222> LOCATION: (344)..(348)
<223> OTHER INFORMATION: n is a, g, c, or t
<220> FEATURE:
<221> NAME/KEY: misc_feature
<222> LOCATION: (352)..(352)
<223> OTHER INFORMATION: n is a, g, c, or t
<220> FEATURE:
<221> NAME/KEY: misc_feature
<222> LOCATION: (359)..(359)
<223> OTHER INFORMATION: n is a, g, c, or t

<400> SEQUENCE: 60
cagcggaaac gctaccggaa cgatgaccgg tcagcaccag aggagtccaa gagagcaccg      60
gactctgatc cagcggtatt agcactgttc cttgttatgc cayggcccct tattatgcct     120
ctgtggacca gnnntgannn tcatgaaaca ttcgacattt cgtttacagg agaagaatcc     180
tagattccgt gagaaaggtg actctgacga agaagaggat gactacgacg gcaaacgtcg     240
tcgctaaagc tgtggaacag cckttgctac tacatgcagc tgttctggtg tccagwcgtt     300
gcagaagagt ccacagytag cagcagtatc cnratctcgc cntnnnnnac ancagattna     360
attcttcggt cggccattcc tcctttc                                         387

<210> SEQ ID NO 61
<211> LENGTH: 23
<212> TYPE: DNA
<213> ORGANISM: Artificial
<220> FEATURE:
<223> OTHER INFORMATION: Primer

<400> SEQUENCE: 61
ctgatcaaag acggagtgct gga                                              23

<210> SEQ ID NO 62
<211> LENGTH: 15
<212> TYPE: DNA
<213> ORGANISM: Artificial
<220> FEATURE:
<223> OTHER INFORMATION: Primer

<400> SEQUENCE: 62
gctcgctgcc gggca                                                       15

<210> SEQ ID NO 63
<211> LENGTH: 12
<212> TYPE: DNA
<213> ORGANISM: Artificial
<220> FEATURE:
<223> OTHER INFORMATION: Probe

<400> SEQUENCE: 63
cccggggctc ac                                                          12

<210> SEQ ID NO 64
<211> LENGTH: 12
<212> TYPE: DNA
<213> ORGANISM: Artificial
<220> FEATURE:
<223> OTHER INFORMATION: Probe
```

```
<400> SEQUENCE: 64
tccggggctc ac                                                          12

<210> SEQ ID NO 65
<211> LENGTH: 333
<212> TYPE: DNA
<213> ORGANISM: Artificial
<220> FEATURE:
<223> OTHER INFORMATION: SNP consensus
<220> FEATURE:
<221> NAME/KEY: misc_feature
<222> LOCATION: (25)..(25)
<223> OTHER INFORMATION: n is a, g, c, or t
<220> FEATURE:
<221> NAME/KEY: misc_feature
<222> LOCATION: (28)..(28)
<223> OTHER INFORMATION: n is a, g, c, or t
<220> FEATURE:
<221> NAME/KEY: misc_feature
<222> LOCATION: (30)..(30)
<223> OTHER INFORMATION: n is a, g, c, or t
<220> FEATURE:
<221> NAME/KEY: misc_feature
<222> LOCATION: (32)..(32)
<223> OTHER INFORMATION: n is a, g, c, or t

<400> SEQUENCE: 65
cagcgtcgag cagctcaacc tggcnggnan cngcctctac ggycaggtac ccgacgcgct      60
ctgcaagctt gctgggcccg ctggccgcct cgccaacctc acgctgtccg gcaactactt     120
cacatccgcc gggccggcat gcgcggcgct gatcaaagac ggagtgctgg acgtkaagaa     180
caactgcaty ccggggctca ccaaccagag gcgcccsgcs gagtgcgcrg cgttccagag     240
ccaaccaaag acwtgcccgg cagcgagcrc tcaggtkaca tgccccgccg ccgcagcttc     300
caggaacgcg gcggckccag gggagaggaa ggt                                  333

<210> SEQ ID NO 66
<211> LENGTH: 24
<212> TYPE: DNA
<213> ORGANISM: Artificial
<220> FEATURE:
<223> OTHER INFORMATION: Primer

<400> SEQUENCE: 66
gcgggcagtc rcaaataaac caga                                             24

<210> SEQ ID NO 67
<211> LENGTH: 26
<212> TYPE: DNA
<213> ORGANISM: Artificial
<220> FEATURE:
<223> OTHER INFORMATION: Primer

<400> SEQUENCE: 67
tcatcctcat cctgctcaac cttcac                                           26

<210> SEQ ID NO 68
<211> LENGTH: 24
<212> TYPE: DNA
<213> ORGANISM: Artificial
<220> FEATURE:
<223> OTHER INFORMATION: Probe

<400> SEQUENCE: 68
agagataaaa tttccattga tgtt                                             24

<210> SEQ ID NO 69
```

```
<211> LENGTH: 23
<212> TYPE: DNA
<213> ORGANISM: Artificial
<220> FEATURE:
<223> OTHER INFORMATION: Probe

<400> SEQUENCE: 69
ggagataaaa tttccattga tgt                                              23

<210> SEQ ID NO 70
<211> LENGTH: 361
<212> TYPE: DNA
<213> ORGANISM: Artificial
<220> FEATURE:
<223> OTHER INFORMATION: SNP consensus
<220> FEATURE:
<221> NAME/KEY: misc_feature
<222> LOCATION: (334)..(335)
<223> OTHER INFORMATION: n is a, g, c, or t
<220> FEATURE:
<221> NAME/KEY: misc_feature
<222> LOCATION: (337)..(337)
<223> OTHER INFORMATION: n is a, g, c, or t

<400> SEQUENCE: 70
ggtgctttrc gcgggcagtc rcaaataaac cagattttgt gcagctgaac atcaatggaa       60
attttatctc ygatgaaggg gttgatgagg tgaaggaaat tctgaaggct ggtaagaaat      120
ctctrgatgt gctgggccca ctagacgaga atgaacctga tggagagcct gatgatgagg      180
atgcygagga cgatgaggac ragctggatt tgaakctgca gagtgtgaag gttgagcagg      240
atgaggatga ttgacgatcc ttaggttaaa tatctttagc tactcagtaa tcatttggat      300
rtccatgagc tacgcaaact tttaattaaa arrnntntac tgagscttt gcattgtcct      360 g                                                                     361

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71
gcgggcagtc rcaaataaac caga                                             24

<210> SEQ ID NO 72
<211> LENGTH: 26
<212> TYPE: DNA
<213> ORGANISM: Artificial
<220> FEATURE:
<223> OTHER INFORMATION: Primer

<400> SEQUENCE: 72
tcatcctcat cctgctcaac cttcac                                           26

<210> SEQ ID NO 73
<211> LENGTH: 16
<212> TYPE: DNA
<213> ORGANISM: Artificial
<220> FEATURE:
<223> OTHER INFORMATION: Probe

<400> SEQUENCE: 73
tgaggacgat gaggac                                                      16

<210> SEQ ID NO 74
```

```
<211> LENGTH: 15
<212> TYPE: DNA
<213> ORGANISM: Artificial
<220> FEATURE:
<223> OTHER INFORMATION: Probe

<400> SEQUENCE: 74
cgaggacgat gagga                                                     15

<210> SEQ ID NO 75
<211> LENGTH: 361
<212> TYPE: DNA
<213> ORGANISM: Artificial
<220> FEATURE:
<223> OTHER INFORMATION: SNP consensus
<220> FEATURE:
<221> NAME/KEY: misc_feature
<222> LOCATION: (334)..(335)
<223> OTHER INFORMATION: n is a, g, c, or t
<220> FEATURE:
<221> NAME/KEY: misc_feature
<222> LOCATION: (337)..(337)
<223> OTHER INFORMATION: n is a, g, c, or t

<400> SEQUENCE: 75
ggtgctttrc gcgggcagtc rcaaataaac cagattttgt gcagctgaac atcaatggaa    60
attttatctc ygatgaaggg gttgatgagg tgaaggaaat tctgaaggct ggtaagaaat   120
ctctrgatgt gctgggccca ctagacgaga atgaacctga tggagagcct gatgatgagg   180
atgcygagga cgatgaggac ragctggatt tgaakctgca gagtgtgaag gttgagcagg   240
atgaggatga ttgacgatcc ttaggttaaa tatctttagc tactcagtaa tcatttggat   300
rtccatgagc tacgcaaact tttaattaaa arrnntntac tgagsctttt gcattgtcct   360
g                                                                  361

<210> SEQ ID NO 76
<211> LENGTH: 14
<212> TYPE: DNA
<213> ORGANISM: Artificial
<220> FEATURE:
<223> OTHER INFORMATION: Primer

<400> SEQUENCE: 76
gcgggcccct cccc                                                      14

<210> SEQ ID NO 77
<211> LENGTH: 20
<212> TYPE: DNA
<213> ORGANISM: Artificial
<220> FEATURE:
<223> OTHER INFORMATION: Primer

<400> SEQUENCE: 77
cgaaccgggy ggsagttccc                                                20

<210> SEQ ID NO 78
<211> LENGTH: 13
<212> TYPE: DNA
<213> ORGANISM: Artificial
<220> FEATURE:
<223> OTHER INFORMATION: Probe

<400> SEQUENCE: 78
gaaatcggcg ccg                                                       13

<210> SEQ ID NO 79
```

```
<211> LENGTH: 13
<212> TYPE: DNA
<213> ORGANISM: Artificial
<220> FEATURE:
<223> OTHER INFORMATION: Probe

<400> SEQUENCE: 79
aaaatcggcg ccg                                                          13

<210> SEQ ID NO 80
<211> LENGTH: 364
<212> TYPE: DNA
<213> ORGANISM: Artificial
<220> FEATURE:
<223> OTHER INFORMATION: SNP consensus
<220> FEATURE:
<221> NAME/KEY: misc_feature
<222> LOCATION: (278)..(287)
<223> OTHER INFORMATION: n is a, g, c, or t
<220> FEATURE:
<221> NAME/KEY: misc_feature
<222> LOCATION: (310)..(315)
<223> OTHER INFORMATION: n is a, g, c, or t

<400> SEQUENCE: 80
gcgagatgtt cttcgccccg caccgcgcgg cccgcggcgg cgctggcgat gcccgcgggc        60
ccctcccctt ttccgggttc ttcaacagct tcgacggcgc cgatttygac gacgacgacc      120
tcgcctgagg gaactsccrc ccggttcggt aacggatgtt gttcgtggat cgcgaatcgt      180
gttatgtcga taccgtgatg gggtctctta attagcgcat cgattcagac tcgtttgggc      240
aatctgaaga tgtttaggga tcaacattac ctttgtgnnn nnnnnnngcc tatggttcgt      300
ggatgcacan nnnngggat caatataagt acctttgtgc cccatggttc gtggatcact      360
gtgc                                                                   364

<210> SEQ ID NO 81
<211> LENGTH: 24
<212> TYPE: DNA
<213> ORGANISM: Artificial
<220> FEATURE:
<223> OTHER INFORMATION: Primer

<400> SEQUENCE: 81
gccgatcact gyccgctagt ttac                                              24

<210> SEQ ID NO 82
<211> LENGTH: 15
<212> TYPE: DNA
<213> ORGANISM: Artificial
<220> FEATURE:
<223> OTHER INFORMATION: Primer

<400> SEQUENCE: 82
gcgggcaacc ccacc                                                        15

<210> SEQ ID NO 83
<211> LENGTH: 16
<212> TYPE: DNA
<213> ORGANISM: Artificial
<220> FEATURE:
<223> OTHER INFORMATION: Probe

<400> SEQUENCE: 83
agttacatac gccacg                                                       16

<210> SEQ ID NO 84
```

```
<211> LENGTH: 16
<212> TYPE: DNA
<213> ORGANISM: Artificial
<220> FEATURE:
<223> OTHER INFORMATION: Probe

<400> SEQUENCE: 84
ggttacatac gccacg                                                        16

<210> SEQ ID NO 85
<211> LENGTH: 374
<212> TYPE: DNA
<213> ORGANISM: Artificial
<220> FEATURE:
<223> OTHER INFORMATION: SNP consensus

<400> SEQUENCE: 85
gcagctcggc gtcaggtcyt ggcccaagtg agcaccgctg ccgccgatca ctgyccgcta         60
gtttacttct tggtytctcg tccccagctc ctgatcgccg tggcgtatgt aacygctgcc        120
gtgcgtgtgc aggtggggtt gcccgccggg gaagttcccg gtgaagttcg acgcgcggca        180
gacgtgctac ctgctcaagg gcaaggtgcg ggcgcacatc aagggtcgt cggagtgcgt         240 ggagttcggc gccggcgacc tcgtcgtctt ccccaagggk ctcagctgca cctgggacgt        300
cgccgccgcc gtcgacaagt actacaagtt cgactcgtcc tgacggctga cgcacatcgc        360
tcccgcccgg ctcc                                                         374

<210> SEQ ID NO 86
<211> LENGTH: 20
<212> TYPE: DNA
<213> ORGANISM: Artificial
<220> FEATURE:
<223> OTHER INFORMATION: Primer

<400> SEQUENCE: 86
cctagtagac ctcaccgcca                                                    20

<210> SEQ ID NO 87
<211> LENGTH: 18
<212> TYPE: DNA
<213> ORGANISM: Artificial
<220> FEATURE:
<223> OTHER INFORMATION: Primer

<400> SEQUENCE: 87
ggagttcacc gatggcac                                                      18

<210> SEQ ID NO 88
<211> LENGTH: 24
<212> TYPE: DNA
<213> ORGANISM: Artificial
<220> FEATURE:
<223> OTHER INFORMATION: Primer

<400> SEQUENCE: 88
cgtcaaacgg catctggaaa ggct                                               24

<210> SEQ ID NO 89
<211> LENGTH: 24
<212> TYPE: DNA
<213> ORGANISM: Artificial
<220> FEATURE:
<223> OTHER INFORMATION: Primer

<400> SEQUENCE: 89
```
agccaaccga acaacaagcc tttc                                          24

<210> SEQ ID NO 90
<211> LENGTH: 24
<212> TYPE: DNA
<213> ORGANISM: Artificial
<220> FEATURE:
<223> OTHER INFORMATION: Primer

<400> SEQUENCE: 90
ccgaaaaccc attcttctag catc                                          24

<210> SEQ ID NO 91
<211> LENGTH: 24
<212> TYPE: DNA
<213> ORGANISM: Artificial
<220> FEATURE:
<223> OTHER INFORMATION: Primer

<400> SEQUENCE: 91
gtgcggtgtt ctctctttca ctct                                          24

<210> SEQ ID NO 92
<211> LENGTH: 25
<212> TYPE: DNA
<213> ORGANISM: Artificial
<220> FEATURE:
<223> OTHER INFORMATION: Primer

<400> SEQUENCE: 92
tctgatctct tcggtgctag agaaa                                         25

<210> SEQ ID NO 93
<211> LENGTH: 24
<212> TYPE: DNA
<213> ORGANISM: Artificial
<220> FEATURE:
<223> OTHER INFORMATION: Primer

<400> SEQUENCE: 93
aagagatctc ccaaccctaa ctgc                                          24

<210> SEQ ID NO 94
<211> LENGTH: 20
<212> TYPE: DNA
<213> ORGANISM: Artificial
<220> FEATURE:
<223> OTHER INFORMATION: Primer

<400> SEQUENCE: 94
acgaggctct tccgagttcc                                               20

<210> SEQ ID NO 95
<211> LENGTH: 22
<212> TYPE: DNA
<213> ORGANISM: Artificial
<220> FEATURE:
<223> OTHER INFORMATION: Primer

<400> SEQUENCE: 95
gtttgaggtg ttcacgggtt ct                                            22

<210> SEQ ID NO 96
<211> LENGTH: 18
<212> TYPE: DNA
<213> ORGANISM: Artificial
<220> FEATURE:

```
<223> OTHER INFORMATION: Primer

<400> SEQUENCE: 96
ccacgcacct cttgtaac                                                    18

<210> SEQ ID NO 97
<211> LENGTH: 18
<212> TYPE: DNA
<213> ORGANISM: Artificial
<220> FEATURE:
<223> OTHER INFORMATION: Primer

<400> SEQUENCE: 97
gggaacctac agcttggt                                                    18

<210> SEQ ID NO 98
<211> LENGTH: 26
<212> TYPE: DNA
<213> ORGANISM: Artificial
<220> FEATURE:
<223> OTHER INFORMATION: Primer

<400> SEQUENCE: 98
ctcttcgatc tttaagagag agagag                                           26

<210> SEQ ID NO 99
<211> LENGTH: 22
<212> TYPE: DNA
<213> ORGANISM: Artificial
<220> FEATURE:
<223> OTHER INFORMATION: Primer

<400> SEQUENCE: 99
acacgaggca ctggtactaa cg                                               22

<210> SEQ ID NO 100
<211> LENGTH: 24
<212> TYPE: DNA
<213> ORGANISM: Artificial
<220> FEATURE:
<223> OTHER INFORMATION: Primer

<400> SEQUENCE: 100
cttgggttct tctctcctat gggt                                             24

<210> SEQ ID NO 101
<211> LENGTH: 24
<212> TYPE: DNA
<213> ORGANISM: Artificial
<220> FEATURE:
<223> OTHER INFORMATION: Primer

<400> SEQUENCE: 101
cgctacaaac aagtggcgtt taat                                             24

<210> SEQ ID NO 102
<211> LENGTH: 316
<212> TYPE: DNA
<213> ORGANISM: Zea mays

<400> SEQUENCE: 102
acctagggac aagaggtgtc ggataagcct agtgacgcta gatcttactg agcgtgtatc      60
ttctcttggt cgttgtgctg actcccaata tcttatcctc ccatctcgtc taatcagggt     120
taatgcatag cgaatggagt aggttgcgac atagtctgat acgctaccgt gcgtaggggt     180
```

```
ggacagtgtc gtcccgtctc ccccacctat ctcttcatac cttgataaca cacaaggaac    240
gataaagtca taaagaaggg tgtctaagcg gcgcatttgg tcaatagtct tgccttggta    300
acgtgcgggt aacagt                                                    316

<210> SEQ ID NO 103
<211> LENGTH: 340
<212> TYPE: DNA
<213> ORGANISM: Zea mays

<400> SEQUENCE: 103
cctggtgaat gaatggttcc atttgactca atagctcata tccctatatc aaaaaaacaa     60
aatcagaacc caaacaacca aaagaccaca aattactaag cacataaaag gaaccatacc    120
tgcttaaaat acctcaaatg ggcatccatc actgcactta ttgattccaa aaattcatac    180
ttcttttttg cttcaatgtt cgcaagggca tgtacctgaa tttcttacag caaagtcaat    240
catcagcaag gctggacagt atacttgcat gtggaaaaat gttgatatac ataccaagtt    300
aaagcgacat ctttcaaaag ctgacttggc attgtgtaga                          340
```

GRAY LEAF SPOT TOLERANT MAIZE AND METHODS OF PRODUCTION

This application claims the benefit of U.S. Provisional Application No. 61/009,697, filed Dec. 31, 2007, the disclosure of which is hereby incorporated in its entirety.

FIELD OF THE INVENTION

This invention relates to Gray Leaf Spot (GLS) tolerant maize plants and a method of producing same. More particularly this invention relates to identifiable genetic material capable of causing tolerance to GLS in maize, and the introgression of this genetic material into maize plants. Additionally, the present invention relates to the introgression of desired genetic material from one or more parent plants into progeny plants with speed, precision, and accuracy.

BACKGROUND OF THE INVENTION

Historically, maize (corn) is an important crop for food, feed, and industrial uses. Any environmental stress factor, e.g. disease, that affects maize can have an impact on maize grain availability for these uses.

Gray Leaf Spot (hereinafter referred to as GLS) has gained prominence the last three decades and is a significant foliar disease in the United States and in other major corn producing areas, such as Mexico, Brazil, Europe, and South Africa. The incidence and severity of GLS appears to be increasing in the United States (Wang et al., Phytopathology 88:1269-75 (1998)), perhaps due to an increase of maize on maize plantings and reduced tillage. These conditions can contribute to overwintering of the fungus and early infection the following season (Laterall and Rossi, Plant Dis. 67:842-37 (1983)). Yield losses in excess of 50% have been reported during GLS epidemics in the United States (Laterall and Rossi, supra; Lipps, Plant Dis. 71:281 (1987)), and estimated losses have been as high as 100% where severe epidemics contributed to increased stalk lodging and early senescence (Laterall and Rossi, supra).

The fungal pathogen *Cercospora zeae-maydis*, which causes GLS, characteristically produces long, rectangular, grayish-tan leaf lesions which run parallel to the leaf veins (Tehon and Daniels, Mycologia 17:240-49 (1925); Latterell and Rossi, supra; Ward et al., Plant Dis. 83:884-95 (1999)). The lesions may blight part or all of the leaf and typically appear in the lower leaves first. Blighting due to GLS is associated with the premature loss of photosynthetic area. The dominant sink of the post-flowering maize plant is the ear, and blighting induces the plant to transfer photosynthate from the stalk and roots to the ear, at high levels, thus causing premature senescence and reduced yield.

The fast and effective development of maize varieties with GLS tolerance is beneficial. The level of tolerance to GLS in commercial hybrids and inbreds differs among varieties. Some varieties exhibiting strong tolerance have been reported. However, the use of phenotypic selection to introgress the GLS trait from a tolerant variety into a susceptible variety can be time consuming and difficult. GLS is sensitive to environmental conditions and requires high humidity and extended leaf wetness. This sensitivity makes it difficult to reliably select for GLS tolerance from year to year based solely on phenotype (Lehmensiek et al., Theor. Appl. Genet. 103:797-803 (2001)). Specialized disease screening sites can be costly to operate, and plants must be grown to maturity in order to classify the level of tolerance. In contrast, selection through the use of molecular markers associated with GLS tolerance has the advantage of permitting at least some selection based solely on the genetic composition of the progeny. Thus, GLS tolerance can be measured very early on in the plant life cycle, even as early as the seed stage. The increased rate of selection that can be obtained through the use of molecular markers associated with the GLS tolerance trait means that plant breeding for GLS tolerance can occur at a faster rate and that commercially acceptable GLS tolerant plants can be developed more quickly.

SUMMARY OF THE INVENTION

Embodiments of this invention are based on the fine mapping of genetic loci significantly correlated with increased GLS tolerance, and the application of this knowledge to plant breeding. Compositions and methods for identifying maize plants with tolerance to GLS are provided. Methods of making maize plants that are tolerant to GLS through marker assisted breeding are provided, as well as plants produced by such methods.

Embodiments include an improved donor variety PHJEP for use as a source of germplasm to introgress tolerance to GLS into maize plants, and progeny derived therefrom. A representative sample of said variety has been deposited with American Type Culture Collection (ATCC) as Accession Number PTA-8851.

One aspect is for a seed of a maize variety designated PHJEP, wherein a representative sample of said maize variety has been deposited as ATCC accession number PTA-8851, or a progeny seed derived therefrom that comprises the PHJEP gray leaf spot tolerance locus and that, when grown, produces a plant that exhibits gray leaf spot tolerance. Plants produced from PHJEP seed or the seed of its progeny are also of interest, as are cells of those plants.

Embodiments also include the specific recombinant chromosomal interval obtained in PHJEP correlated with enhanced GLS tolerance, and the introgression of this chromosomal interval into other varieties and plants. Some embodiments include the introgression of unique haplotypes of PHJEP into other varieties and plants.

In one aspect, the PHJEP gray leaf spot tolerance locus in the progeny seed is located on a PHJEP-derived chromosomal interval comprising a chromosomal region of PHJEP defined by UMC1346 and UMC1702. In another, the PHJEP gray leaf spot tolerance locus in the progeny seed is defined by a haplotype comprising: allele G at PHM 00045-01, allele A at PHM 00043-01, allele A at PHM 15534-13, allele G at PHM 04694-10, allele T at PHM 01811-32, allele T at PHM 01963-15, allele C at PHM 01963-22, allele T at PHM 05013-12, allele T at PHM 00586-10, allele A at PHM 00049-01. In still another aspect, the PHJEP gray leaf spot tolerance locus is defined by a haplotype comprising: allele G at PHM 00045-01, allele A at PHM 00043-01, allele C at PHM 01963-22, and allele T at PHM 05013-12.

In other aspects, the progeny seed is a backcross conversion of the PHJEP gray leaf spot tolerance locus. Also of interest is a progeny seed that is a backcross conversion produced with a recurrent parent selected from PHVNV, PHW3Y, PHVRA, PHEWB, and PHWRC.

In other aspects the progeny seed is a hybrid variety, and at least one inbred parent of the hybrid variety is a backcross conversion of the PHJEP gray leaf spot tolerance locus into a recurrent parent selected from PHVNV, PHW3Y, PHVRA, PHEWB, and PHWRC.

Other embodiments include a process for identifying a first corn plant comprising a locus correlated with gray leaf spot tolerance, said process comprising: (a) obtaining a first genetic profile of said first corn plant for the chromosomal interval on chromosome 4 between BNLG1755 and UMC1299, (b) obtaining a second genetic profile from a second corn plant comprising the locus correlated with gray leaf spot tolerance, wherein the locus is located on chromosome 4 between BNLG1755 and UMC1299, and (c) comparing said first genetic profile with said second genetic profile.

In another aspect, the process further comprises selecting said first corn plant if it comprises the locus correlated with gray leaf spot tolerance.

In addition, the second genetic profile can be the genetic profile of PHJEP or a progeny of PHJEP, or can comprise one or more marker alleles selected from the group consisting of: allele G at PHM 00045-01, allele A at PHM 00043-01, allele A at PHM 15534-13, allele G at PHM 04694-10, allele T at PHM 01811-32, allele T at PHM 01963-15, allele C at PHM 01963-22, allele T at PHM 05013-12, allele T at PHM 00586-10, and allele A at PHM 00049-01.

The second genetic profile can also comprise one or more marker alleles selected from the group consisting of: allele G at PHM 00045-01, allele A at PHM 00043-01, allele C at PHM 01963-22, and allele T at PHM 05013-12.

In other aspects, the genetic profiles can be determined for the chromosomal interval on chromosome 4 between BNLG1755 and MMC0371. In addition, the locus correlated with gray leaf spot tolerance can be PHM 15534, PHM 04694, PHM 01811, PHM 01963, PHM 05013, or PHM 00586.

Also of interest are corn plants identified by the process and cells and seeds of those corn plants.

A further embodiment includes a process for identifying a first corn plant comprising a locus correlated with gray leaf spot tolerance, said process comprising: (a) obtaining a first genetic profile of said first corn plant for the chromosomal interval on chromosome 4 delineated by and including SEQ ID NO:102, or a nucleotide sequence that is 95% identical to SEQ ID NO:102 based on the Clustal V method of alignment, and SEQ ID NO:103, or a nucleotide sequence that is 95% identical to SEQ ID NO:103 based on the Clustal V method of alignment, (b) obtaining a second genetic profile from a second corn plant comprising the locus correlated with gray leaf spot tolerance, wherein the locus is in said interval, and (c) comparing said first genetic profile with said second genetic profile.

Other embodiments include a corn seed comprising a haplotype of: allele G at PHM 00045-01, allele A at PHM 00043-01, allele A at PHM 15534-13, allele G at PHM 04694-10, allele T at PHM 01811-32, allele T at PHM 01963-15, allele C at PHM 01963-22, allele T at PHM 05013-12, allele T at PHM 00586-10, allele A at PHM 00049-01; and a corn seed comprising a haplotype of: allele G at PHM 00045-01, allele A at PHM 00043-01, allele C at PHM 01963-22, and allele T at PHM 05013-12. Also of interest are plants produced by the corn seeds.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

The term "maize" includes any member of the species *Zea mays*. "Maize" and "corn" are used interchangeably herein.

A "seed" is a small embryonic plant enclosed in a protective seed coat. It is the product of the ripened plant ovule generated after fertilization.

"Germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

"Variety", when used in conjunction with plants, encompasses botanical and cultivated plants, including inbreds and hybrids, and means a plant grouping within a single botanical taxon of the lowest known rank, where the grouping can be defined by the expression of characteristics resulting from a given genotype or combination of genotypes.

The term "inbred" means a substantially homozygous variety.

The term "hybrid" means any offspring/progeny of a cross between two genetically unlike individuals, including a cross of two different inbred lines.

The term "allele" refers to one of two or more different nucleotide sequences that occur at a specific locus.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

A "favorable allele" is the allele at a particular locus that confers, or contributes to, an agronomically desirable phenotype, e.g., tolerance to GLS, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indicator that the desired trait or trait form will occur in a plant comprising the allele. An allele "negatively" correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes).

An individual is "heterozygous" if more than one allele type is present at a given locus (e.g., a diploid individual with one copy each of two different alleles).

A special case of a heterozygous situation is where one chromosome has an allele of a gene and the other chromosome lacks the gene, locus, or region completely—in other words, has a deletion relative to the first chromosome. This situation is referred to as "hemizygous".

The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene, or marker is located. Thus, for example, a "gene locus" is a specific chromosome location in the genome of a species where a specific gene can be found. A locus correlated with GLS tolerance denotes a region on the genome that is directly related to a phenotypically quantifiable GLS tolerance trait.

A "genetic complement" has at least one set or ploidy of alleles. For example, a single cross hybrid inherits two genetic complements, one from each inbred parent.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A large number of maize molecular markers are known in the art, and are published or available from various sources, such as the Maize GDB internet resource and the Arizona Genomics Institute internet resource run by the University of Arizona. Similarly, numerous methods for detecting molecular markers are well established.

A "polymorphism" is a variation in the DNA that is too common to be due merely to new mutation (i.e. occurs at a frequency of at least 1% in a population). Any differentially inherited polymorphic trait (including nucleic acid polymorphism) that segregates among progeny is a potential marker. The genomic variability can be of any origin, for example, insertions, deletions, duplications, repetitive elements, point mutations, recombination events, or the presence and sequence of transposable elements.

A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules.

A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus.

A "marker allele", alternatively an "allele of a marker locus", is one of a plurality of polymorphic nucleotide sequences found at a marker locus in a population that is polymorphic for the marker locus. In some aspects, the present invention provides marker loci correlating with tolerance to GLS in maize. Each of the identified markers is expected to be in close physical and genetic proximity (resulting in physical and/or genetic linkage) to a genetic element, e.g., a QTL, that contributes to GLS tolerance.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. The term "Genetic Marker" can refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, *Trends in Genetics* 9:275-280), Amplified Fragment Length Polymorphism (AFLP) (Vos et al, 1995, *Nucleic Acids Res.* 23:4407-4414), Single Nucleotide Polymorphism (SNP) (Brookes, 1999, *Gene* 234:177-186), Sequence Characterized Amplified Region (SCAR) (Paran and Michelmore, 1993, *Theor. Appl. Genet.* 85:985-993), Sequence Tagged Site (STS) (Onozaki et al., 2004, *Euphytica* 138:255-262), Single Stranded Conformation Polymorphism (SSCP) (Orita et al., 1989, *Proc Natl Acad Sci USA* 86:2766-2770), Inter-Simple Sequence Repeat (ISSR) (Blair et al., 1999, *Theor. Appl. Genet.* 98:780-792), Inter-Retrotransposon Amplified Polymorphism (IRAP), Retrotransposon-Microsatellite Amplified Polymorphism (REMAP) (Kalendar et al., 1999, *Theor. Appl. Genet.* 98:704-711), an RNA cleavage product (such as a Lynx tag), and the like.

The term "indel" refers to an insertion or deletion, wherein one line may be referred to as having an insertion relative to a second line, or the second line may be referred to as having a deletion relative to the first line.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD). Methods of mapping a gene via cleaved amplified polymorphic sequences (CAPS) are also well-known (see, e.g., Konieczny & Ausubel, Plant J. 4:403-10 (1993)).

"Marker assisted selection" (or MAS) is a process by which phenotypes are selected based on marker genotypes.

"Marker assisted counter-selection" is a process by which marker genotypes are used to identify plants that will not be selected, allowing them to be removed from a breeding program or planting.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "genetic map" is a description of genetic linkage relationships among loci on one or more chromosomes (or linkage groups) within a given species, generally depicted in a diagrammatic or tabular form. The loci are genetic landmarks, or markers, and for each genetic map, distances between markers are measured by the recombination frequencies between them. A genetic map is a product of the mapping population, types of markers used, and the polymorphic potential of each marker between different populations. The order and genetic distances between loci can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maizeGDB). However, information can be correlated from one map to another using a general framework of common markers. One of ordinary skill in the art can use the framework of common markers to identify the positions of markers and other loci of interest on each individual genetic map.

"Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species.

A "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

"Recombination" is an exchange of segments of homologous chromosomes during meiosis whereby linked genes become recombined; also refers to the product of such exchange.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

"Genome" refers to the total DNA, or the entire set of genes, carried by a chromosome or chromosome set.

As used herein, the term "linkage" is used to describe the degree with which one marker locus is "associated with" another marker locus or some other locus (for example, a tolerance locus). The closer two marker loci lie on the same chromosome, the more closely they will be associated in gametes and the more often they will appear together; marker loci that are very close are essentially never separated because it is extremely unlikely that a crossover point will occur between them.

As used herein, "linkage equilibrium" describes a situation where two markers independently segregate, i.e., sort among progeny randomly. Markers that show linkage equilibrium are considered unlinked (whether or not they lie on the same chromosome).

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked.

Linkage disequilibrium is most commonly assessed using the measure $r^2$, which is calculated using the formula described by Hill, W. G. and Robertson, A, *Theor. Appl. Genet.* 38:226-231 (1968). When $r^2=1$, complete LD exists between the two marker loci, meaning that the markers have not been separated by recombination and have the same allele frequency. Values for $r^2$ above 1/3 indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic tolerance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be closely linked to each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to tolerance and a closely linked marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the linked marker locus, and the two "favorable" alleles are not inherited together (i.e., the two loci are "out of phase" with each other).

As used herein, the terms "chromosome interval", "chromosomal interval", "chromosome segment", or "chromosomal segment" designate a contiguous linear span of genomic DNA that resides in planta on a single chromosome, usually defined with reference to two markers defining the end points of the chromosomal interval. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "Gray Leaf Spot" or "GLS" refers to a cereal disease caused by the fungal pathogen *Cercospora zeae-maydis*, which characteristically produces long, rectangular, grayish-tan leaf lesions which run parallel to the leaf vein.

"Newly conferred tolerance" or "enhanced tolerance" in a maize plant to GLS is an indication that the maize plant is less affected with respect to yield and/or survivability or other relevant agronomic measures, upon introduction of the causative agents of that disease, e.g., *Cercospora zeae-maydis*. Tolerance is a relative term, indicating that the infected plant produces better yield of maize than another, similarly treated, more susceptible plant. That is, the conditions cause a reduced decrease in maize survival and/or yield in a tolerant maize plant, as compared to a susceptible maize plant.

One of skill will appreciate that maize plant tolerance to GLS varies widely, can represent a spectrum of more tolerant or less tolerant phenotypes, and can vary depending on the severity of the infection. However, by simple observation, one of skill can determine the relative tolerance or susceptibility of different plants, plant lines or plant families to GLS, and furthermore, will also recognize the phenotypic gradations of "tolerant". For example, a 1 to 9 visual rating indicating the tolerance to GLS can be used. A higher score indicates a higher resistance. Data should be collected only when sufficient selection pressure exists in the experiment measured.

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "backcross conversion" is a product of introgression of a locus or trait into a variety by backcrossing.

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) *Marker-assisted Selection in Backcross Breeding, Analysis of Molecular Marker Data*, pp. 41-43. The initial cross gives rise to the F1 generation; the term "BC1" then refers to the second use of the recurrent parent, "BC2" refers to the third use of the recurrent parent, and so on.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

An "ancestral line" is a parent line used as a source of genes e.g., for the development of elite lines. An "ancestral population" is a group of ancestors that have contributed the bulk of the genetic variation that was used to develop elite lines. "Progeny" are the descendants of ancestors, and may be separated from their ancestors by many generations of breeding. For example, elite lines are the progeny of their ancestors. A "pedigree structure" defines the relationship between a progeny and each ancestor that gave rise to that descendant. A pedigree structure can span one or more generations, describing relationships between the progeny and its parents, grand parents, great-grand parents, etc.

An "elite line" or "elite strain" is an agronomically superior line that has resulted from many cycles of breeding and selection for superior agronomic performance. Numerous elite lines are available and known to those of skill in the art of maize breeding. An "elite population" is an assortment of elite individuals or lines that can be used to represent the state of the art in terms of agronomically superior genotypes of a given crop species, such as maize. Similarly, an "elite germplasm" or elite strain of germplasm is an agronomically superior germplasm, typically derived from and/or capable of giving rise to a plant with superior agronomic performance, such as an existing or newly developed elite line of maize.

In contrast, an "exotic maize strain" or an "exotic maize germplasm" is a strain or germplasm derived from maize that does not belong to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR), and RNA polymerase based amplification (e.g., by transcription) methods.

An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from its natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference.

The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection", "transformation", and "transduction".

As used herein, the term "vector" is used in reference to polynucleotide or other molecules that transfer nucleic acid segment(s) into a cell. The term "vehicle" is sometimes used interchangeably with "vector". A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals, and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Positional cloning" is a cloning procedure in which a target nucleic acid is identified and isolated by its genomic proximity to marker nucleic acid. For example, a genomic nucleic acid clone can include part or all of two more chromosomal regions that are closely linked to one another. If a marker can be used to identify the genomic nucleic acid clone from a genomic library, standard methods such as sub-cloning or sequencing can be used to identify and/or isolate subsequences of the clone that are located near the marker.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

A "haplotype" is the genotype of an individual at a plurality of genetic loci. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment. The former can also be referred to as "marker haplotypes" or "marker alleles", while the latter can be referred to as "long-range haplotypes".

The terms "phenotype", or "phenotypic trait" or "trait" refers to one or more trait of an organism. The phenotype can be observable to the naked eye, or by any other means of evaluation known in the art, e.g., microscopy, biochemical analysis, genomic analysis, or an assay for a particular disease tolerance. In some cases, a phenotype is directly controlled by a single gene or genetic locus, i.e., a "single gene trait". In other cases, a phenotype is the result of several genes.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

A "representative sample" is a sample that encompasses the relevant composition and characteristics of the population sampled.

A "centromere" is the single site on each chromosome for kinetochore assembly and proper chromosome segregation in mitosis and meiosis.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability, and the like. Yield is, therefore, the final culmination of all agronomic traits.

A "set" of markers or probes refers to a collection or group of markers or probes, or the data derived therefrom, used for a common purpose, e.g., identifying maize plants with a desired trait (e.g., tolerance to GLS). Frequently, data corresponding to the markers or probes, or data derived from their use, is stored in an electronic medium. While each of the members of a set possess utility with respect to the specified purpose, individual markers selected from the set as well as subsets including some, but not all, of the markers are also effective in achieving the specified purpose.

A "genetic profile" is an identification and characterization of sequences diagnostic for a particular trait or locus.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "contig" refers to a set of overlapping DNA segments derived from a single genetic source. A contig map depicts the relative order of a linked library of contigs representing an extended chromosome segment. A "public contig" is a publicly available set of overlapping DNA segments derived from a single genetic source. Examples of public sources include the Maize Mapping Project (University of Missouri—Columbia, University of Georgia, and University of Arizona), the Arizona Genomics Institute, the MaizeGDB website, and the Maize Sequence website. Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley, or sorghum.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4, and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer and the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

BRIEF DESCRIPTION OF THE DRAWINGS AND SEQUENCES

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the final location of the PHJEP GLS QTL on the IBM2 2004 neighbors chromosome 4 map. Distances are in cM.

FIG. 2 shows a close-up of the GLS QTL on the IBM2 2004 neighbors chromosome 4 map after the second round of mapping. Boxed markers were used in the second round of QTL mapping. Arrow shows QTL region after this second round of QTL mapping. Black-filled box shows final QTL location after fine mapping.

FIG. 3 shows the GLS QTL map location after fine mapping.

FIGS. 4A-F show the physical map arrangement of sequenced BACs (obtained from the Maize Genome Browser, which is publicly available on the internet in the chromosome 4 region containing the GLS QTL.

FIG. 5 shows introgression of the GLS QTL into PHN46. Dark gray indicates PH14T origin. Horizontal lines indicate PHN46 origin. Diagonal lines indicate region of recombination. *Location for UMC1299 taken from IBM2 Neighbors frame map—concordant with physical map location.

FIG. 6 shows levels of disease resistance to GLS in PHN46 (left), PH14T (middle) and PHJEP (right).

FIG. 7 shows levels of disease resistance to GLS in A) a Pioneer hybrid with the QTL introgression, created by a cross between inbreds PHP38 and PHJEP, and in B) Pioneer hybrid 3394 with no QTL introgression.

FIG. 8 shows further introgression of the GLS QTL into elite materials. Dark gray indicates PH14T origin. Horizontal lines indicate PHN46 origin. Diagonal lines indicate recombination between PHJEP and new elite germplasm. Dots indicate recombination between PH14T and PHN46. Unshaded indicates new elite germplasm PHVNV, PHEHG, PHW3Y, PHEWB, or PHWRC.

FIG. 9 provides a table listing genomic and SSR markers, including those markers that demonstrated linkage disequilibrium with the GLS tolerance phenotype (directly or by extrapolation from the genetic map). The table provides the sequences of the left and right PCR primers used in the SSR marker locus genotyping analysis. Also shown is the number of nucleotides in the tandem repeating element in the SSR.

FIG. 10 provides a table listing the SNP markers that demonstrated linkage disequilibrium with the GLS tolerance phenotype. The table provides the sequences of the PCR primers used to generate a SNP-containing amplicon.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

SEQ ID NO:1 and SEQ ID NO:2 are the primers designed to amplify BAC end bacm2.pk027.h10.f.

SEQ ID NO:3 and SEQ ID NO:4 are the primers designed to amplify BAC end bacm.pk098.d7.

SEQ ID NO:5 and SEQ ID NO:6 are the primers designed to amplify BAC end bacm.pk106.j3.

SEQ ID NO:7 and SEQ ID NO:8 are the primers designed to amplify BAC end bacm.pk018.h15.

SEQ ID NO:9 and SEQ ID NO:10 are the primers designed to amplify BAC end bacm.pk040.o17. The primer pair represents a CAPs marker referred to herein as PHM 00045.

SEQ ID NO:11 and SEQ ID NO:12 are the primers designed to amplify BAC end bacm2.pk065.b22.f.

SEQ ID NO:13 and SEQ ID NO:14 are the primers designed to amplify BAC end bacb.pk0333.o19. The primer pair represents a CAPs marker referred to herein as PHM 00043.

SEQ ID NO:15 and SEQ ID NO:16 are the primers designed to amplify BAC end bacc.pk0267.m12.f.

SEQ ID NO:17 and SEQ ID NO:18 are the primers designed to amplify the EST overgo probe cl33021_1.

SEQ ID NO:19 and SEQ ID NO:20 are the primers designed to amplify BAC end bacb.pk0241.h17.f.

SEQ ID NO:21 and SEQ ID NO:22 are the primers designed to amplify clone chp2.pk0007.d2.

SEQ ID NO:23 and SEQ ID NO:24 are the primers designed to amplify BAC end bacc.pk0530.f13.f.

SEQ ID NO:25 and SEQ ID NO:26 are the primers designed to clone p0094.csstg88.

SEQ ID NO:27 and SEQ ID NO:28 are the primers designed to amplify BAC end bacb.pk0269.n19.

SEQ ID NO:29 and SEQ ID NO:30 are the primers designed to amplify BAC end bacb.pk0009.b21.f.

SEQ ID NO:31 and SEQ ID NO:32 are the primers designed to amplify BAC end bacb.pk0117.i09.f.

SEQ ID NO:33 and SEQ ID NO:34 are the primers designed to amplify BAC end bacc.pk0280.n12.

SEQ ID NO:35 and SEQ ID NO:36 are the primers designed to amplify BAC end bacb.pk0219.j20.

SEQ ID NO:37 and SEQ ID NO:38 are the primers designed to amplify BAC end bacc.pk0132.b16.f.

SEQ ID NO:39 and SEQ ID NO:40 are the primers designed to amplify BAC end bacb.pk0221.o22.

SEQ ID NO:41 and SEQ ID NO:42 are the primers designed to amplify BAC end bacb.pk0544.j18.

SEQ ID NO:43 and SEQ ID NO:44 are the primers designed to amplify BAC end bacb.pk0540.c18.f.

SEQ ID NO:45 and SEQ ID NO:46 are the primers designed to amplify BAC end bacm.pk022.b8. The primer pair represents a CAPs marker referred to herein as PHM 00049.

SEQ ID NO:47 and SEQ ID NO:48 are the primers for marker locus PHM 7245.

SEQ ID NO:49 is the annotated nucleotide sequence of a putative R gene of the type classified as an LRR-like protein kinase.

SEQ ID NO:50 is the amino acid sequence of the protein encoded by SEQ ID NO:49.

SEQ ID NO:51 is the sequence of the PHM 15534-13 forward primer.

SEQ ID NO:52 is the sequence of the PHM 15534-13 reverse primer.

SEQ ID NO:53 is the sequence of the PHM 15534-13 probe 1.

SEQ ID NO:54 is the sequence of the PHM 15534-13 probe 2.

SEQ ID NO:55 is the sequence of the PHM 15534 reference sequence.

SEQ ID NO:56 is the sequence of the PHM 04694-10 forward primer.

SEQ ID NO:57 is the sequence of the PHM 04694-10 reverse primer.

SEQ ID NO:58 is the sequence of the PHM 04694-10 probe 1.

SEQ ID NO:59 is the sequence of the PHM 04694-10 probe 2.

SEQ ID NO:60 is the sequence of the PHM 04694-10 reference sequence.

SEQ ID NO:61 is the sequence of the PHM 01811-32 forward primer.

SEQ ID NO:62 is the sequence of the PHM 01811-32 reverse primer.

SEQ ID NO:63 is the sequence of the PHM 01811-32 probe 1.

SEQ ID NO:64 is the sequence of the PHM 01811-32 probe 2.

SEQ ID NO:65 is the sequence of the PHM 01811-32 reference sequence.

SEQ ID NO:66 is the sequence of the PHM 01963-15 forward primer.

SEQ ID NO:67 is the sequence of the PHM 01963-15 reverse primer.

SEQ ID NO:68 is the sequence of the PHM 01963-15 probe 1.

SEQ ID NO:69 is the sequence of the PHM 01963-15 probe 2.

SEQ ID NO:70 is the sequence of the PHM 01963-15 reference sequence.

SEQ ID NO:71 is the sequence of the PHM 01963-22 forward primer.

SEQ ID NO:72 is the sequence of the PHM 01963-22 reverse primer.

SEQ ID NO:73 is the sequence of the PHM 01963-22 probe 1.

SEQ ID NO:74 is the sequence of the PHM 01963-22 probe 2.

SEQ ID NO:75 is the sequence of the PHM 01963-22 reference sequence.

SEQ ID NO:76 is the sequence of the PHM 05013-12 forward primer.

SEQ ID NO:77 is the sequence of the PHM 05013-12 reverse primer.

SEQ ID NO:78 is the sequence of the PHM 05013-12 probe 1.

SEQ ID NO:79 is the sequence of the PHM 05013-12 probe 2.

SEQ ID NO:80 is the sequence of the PHM 05013-12 reference sequence.

SEQ ID NO:81 is the sequence of the PHM 00586-10 forward primer.

SEQ ID NO:82 is the sequence of the PHM 00586-10 reverse primer.

SEQ ID NO:83 is the sequence of the PHM 00586-10 probe 1.

SEQ ID NO:84 is the sequence of the PHM 00586-10 probe 2.

SEQ ID NO:85 is the sequence of the PHM 00586-10 reference sequence.

SEQ ID NO:86 is the sequence of the left primer for marker bnlg1755.

SEQ ID NO:87 is the sequence of the right primer for marker bnlg1755.

SEQ ID NO:88 is the sequence of the left primer for marker umc156a.

SEQ ID NO:89 is the sequence of the right primer for marker umc156a.

SEQ ID NO:90 is the sequence of the left primer for marker umc1142.

SEQ ID NO:91 is the sequence of the right primer for marker umc1142.

SEQ ID NO:92 is the sequence of the left primer for marker umc1346.

SEQ ID NO:93 is the sequence of the right primer for marker umc1346.

SEQ ID NO:94 is the sequence of the left primer for marker umc1702.

SEQ ID NO:95 is the sequence of the right primer for marker umc1702.

SEQ ID NO:96 is the sequence of the left primer for marker mmc0371.

SEQ ID NO:97 is the sequence of the right primer for marker mmc0371.

SEQ ID NO:98 is the sequence of the left primer for marker bnlg1621a.

SEQ ID NO:99 is the sequence of the right primer for marker bnlg1621a.

SEQ ID NO:100 is the sequence of the left primer for marker umc1299.

SEQ ID NO:101 is the sequence of the right primer for marker umc1299.

SEQ ID NO:102 is the sequence of the PHM 00045 reference sequence.

SEQ ID NO:103 is the sequence of the PHM 00049 reference sequence.

DETAILED DESCRIPTION OF THE INVENTION

The identification and selection of maize plants that show tolerance to GLS using MAS can provide an effective and environmentally friendly approach to overcoming losses caused by this disease. The present invention provides maize marker loci that demonstrate statistically significant co-segregation with GLS tolerance. Detection of these loci or additional linked loci can be used in marker assisted maize breeding programs to produce tolerant plants, or plants with improved tolerance to GLS. The linked SSR and SNP markers identified herein are provided below and in the figures. These markers include PHM 15534, PHM 04694, PHM 01811, PHM 01963, PHM 05013, and PHM 00586 (FIG. 10).

Each SSR-type marker displays a plurality of alleles that can be visualized as different sized PCR amplicons. The PCR primers that are used to generate the SSR-marker amplicons are provided in FIG. 9. The alleles of SNP-type markers are determined using an allele-specific hybridization protocol, as known in the art. The PCR primers used to amplify the SNP domain are provided in FIG. 10.

As recognized in the art, any other marker that is linked to a QTL marker (e.g., a disease tolerance marker) also finds use for that same purpose. Examples of additional markers that are linked to the disease tolerance markers recited herein are provided. For example, a linked marker can be determined from the closely linked markers provided in Table 3. It is not intended, however, that linked markers finding use with the invention be limited to those recited in Table 3.

The invention also provides chromosomal QTL intervals that correlate with GLS tolerance. These intervals are located on linkage group 4. Any marker located within these intervals finds use as a marker for GLS tolerance. These intervals include: (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702.

The invention further provides a region of contiguous DNA bounded by and including PHM 00045 (SEQ ID NO:102) and PHM 00049 (SEQ ID NO:103), that houses marker loci that cosegregate with GLS tolerance (FIG. 4). Any marker locus lying within the contiguous span of DNA between and including SEQ ID NO:102, or a nucleotide sequence that is 95% identical to SEQ ID NO:102 based on the Clustal V method of alignment, and SEQ ID NO:103, or a nucleotide sequence that is 95% identical to SEQ ID NO:103 based on the Clustal V method of alignment, can find use as a marker for GLS tolerance.

Methods for identifying maize plants or germplasm that carry preferred alleles of tolerance marker loci are a feature of the invention. In these methods, any of a variety of marker detection protocols can be used to identify alleles at marker loci, depending on the type of marker locus. Typical methods for detection include ASH, SSR detection, RFLP analysis, and many others.

Although particular marker alleles can show co-segregation with a disease tolerance or susceptibility phenotype, it is important to note that the marker locus is not necessarily part of the QTL locus responsible for the tolerance or susceptibility. For example, it is not a requirement that the marker polynucleotide sequence be part of a gene that imparts disease tolerance (for example, be part of the gene open reading frame). The association between a specific marker allele with the tolerance or susceptibility phenotype is due to the original "coupling" linkage phase between the marker allele and the QTL tolerance or susceptibility allele in the ancestral maize line from which the tolerance or susceptibility allele originated. Eventually, with repeated recombination, crossing over events between the marker and QTL locus can change this orientation. For this reason, the favorable marker allele may change depending on the linkage phase that exists within the tolerant parent used to create segregating populations. This does not change the fact that the genetic marker can be used to monitor segregation of the phenotype. It only changes which marker allele is considered favorable in a given segregating population.

Identification of maize plants or germplasm that contain marker alleles associated with improved tolerance provides a basis for performing marker assisted selection of maize. Maize plants that comprise favorable marker alleles are selected for, while maize plants that comprise marker alleles that are negatively correlated with tolerance can be selected against. Desired marker alleles can be introgressed into maize having a desired (e.g., elite or exotic) genetic background to produce an introgressed tolerant maize plant or germplasm. In some aspects, it is contemplated that a plurality of tolerance marker alleles are sequentially or simultaneous selected and/or introgressed. The combinations of tolerance markers that can be used to select for tolerance in a single plant are not limited, and can include any combination of markers recited in FIG. 3, any markers linked to the markers recited in FIG. 3, or any markers located within the QTL intervals defined herein.

As an alternative to standard breeding methods of introducing traits of interest into maize (e.g., introgression), transgenic approaches can also be used. In these methods, exogenous nucleic acids controlling traits of interest, e.g. disease tolerance, can be introduced into target plants or germplasm. Verification of tolerance can be performed by available tolerance protocols (as described, e.g., above). Tolerance assays are useful to verify that the tolerance trait still segregates with the marker in any particular plant or population, and, of course, to measure the degree of tolerance improvement achieved by introgressing or transgenically introducing the trait into a desired background. A plant comprising favorable alleles of a gray leaf spot QTL can have a tolerance score of at least 2.7, 2.6, 2.5, 2.4, 2.3, 2.2, 2.1, 2.0, 1.9, 1.8, or 1.7 points greater, on a one to nine scale, when compared to a near isogenic plant not comprising the favorable alleles of the gray leaf spot QTL. In a 1 to 9 visual rating system, a higher score indicates a higher resistance. Data should be collected only when sufficient selection pressure exists in the experiment measured.

Systems, including automated systems for selecting plants that comprise a marker of interest and/or for correlating presence of the marker with tolerance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also a feature of the invention. For example, a kit can include appropriate primers or probes for detecting tolerance-associated marker loci and instructions in using the primers or probes for detecting the marker loci and correlating the loci with predicted GLS tolerance. The kits can further include packaging materials for packaging the probes, primers or instructions, controls such as control amplification reactions that include probes, primers or template nucleic acids for amplifications, molecular size markers, or the like.

Tolerance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The markers herein, as seen in FIG. 3, e.g., PHM 15534, PHM 04694, PHM 01811, PHM 01963, PHM 05013, and PHM 00586, as well as any of the chromosome intervals (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702, have been found to correlate with newly conferred tolerance, enhanced tolerance, or susceptibility to GLS in maize. This means that the markers are sufficiently closely linked to a tolerance trait that they can be used as predictors for the tolerance trait. This is extremely useful in the context of marker assisted selection (MAS), discussed in more detail herein. In brief, maize plants or germplasm can be selected for marker alleles that positively correlate with tolerance, without actually raising maize and measuring for newly conferred tolerance or enhanced tolerance (or, contrarily, maize plants can be selected against if they possess markers that negatively correlate with newly conferred tolerance or enhanced tolerance). MAS is a powerful shortcut to selecting for desired phenotypes and for introgressing desired traits into cultivars of maize (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the QTL markers are a subset of the markers provided in FIG. 3, for example, markers designed to bacb.pk0333.o19 (e.g., PHM 00043), bacc.pk0267.m12.f, cl133021__1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (e.g., PHM 00049).

When referring to the relationship between two genetic elements, such as a genetic element contributing to tolerance and a closely linked marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the closely linked marker locus, and the two "favorable" alleles are not inherited together (i.e., the two loci are "out of phase" with each other).

A favorable allele of a marker is that allele of the marker that co-segregates with a desired phenotype (e.g., disease tolerance). As used herein, a QTL marker has a minimum of one favorable allele, although it is possible that the marker might have two or more favorable alleles found in the population. Any favorable allele of that marker can be used advantageously for the identification and construction of tolerant maize lines. Optionally, one, two, three or more favorable allele(s) of different markers are identified in, or introgressed into a plant, and can be selected for or against during MAS. Desirably, plants or germplasm are identified that have at least one such favorable allele that positively correlates with newly conferred or enhanced tolerance.

Alternatively, a marker allele that is associated with disease susceptibility also finds use with the invention, since that allele can be used to identify and counter select disease-susceptible plants. Such an allele can be used for exclusionary purposes during breeding to identify plants or germplasm that have alleles that negatively correlate with tolerance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles for tolerance to GLS, or favorable alleles for tolerance to GLS are introgressed into a desired maize germplasm. One of skill in the art recognizes that the simultaneous selection of favorable alleles for GLS tolerance in the same plant is likely to result in an additive (or even synergistic) protective effect for the plant.

One of skill recognizes that, in some cases, the identification of favorable marker alleles is germplasm-specific. The determination of which marker alleles correlate with tolerance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in maize populations other than the populations used or described herein is well within the scope of the invention.

Amplification primers for amplifying SSR-type marker loci are a feature of the invention. Another feature of the invention is primers specific for the amplification of SNP domains (SNP markers), and the probes that are used to genotype the SNP sequences. FIGS. 9 and 10 provide specific primers for marker locus amplification and probes for detecting amplified marker loci. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel") and *PCR Protocols A Guide to Methods and Applications* (Innis et al. eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc. ("Croy").

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, cleaved amplified polymorphic sequences (CAPS) detection, isozyme markers detection, or the like. While the exemplary markers provided in the figures and tables herein are either SSR or SNP (ASH) markers, any of the aforementioned marker types can be employed in the context of the invention to identify chromosome segments encompassing genetic element that contribute to superior agronomic performance (e.g., newly conferred tolerance or enhanced tolerance).

QTL Chromosome Intervals

In some aspects, the invention provides QTL chromosome intervals, where one or more QTL associated with GLS tolerance are contained in those intervals. A variety of methods well known in the art are available for identifying chromosome intervals (described in detail in the Examples below).

The boundaries of such chromosome intervals are drawn to encompass markers that will be linked to one or more QTL. In other words, the chromosome interval is drawn such that any marker that lies within that interval (including the terminal markers that define the boundaries of the interval) can be used as a marker for disease tolerance. Each interval comprises a GLS QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL.

The present invention provides maize chromosome intervals, where the markers within that interval demonstrate co-segregation with tolerance to GLS (see Table 1).

TABLE 1

| Flanking Markers | Method(s) of Identification |
|---|---|
| BNLG1755 and UMC1299 | Linkage to a preferred marker |
| BNLG1755 and BNLG1621A | Linkage to a preferred marker |
| BNLG1755 and MMC0371 | Linkage to a preferred marker |
| BNLG1755 and UMC1702 | Linkage to a preferred marker |
| UMC156A and UMC1299 | Linkage to a preferred marker |
| UMC156A and BNLG1621A | Linkage to a preferred marker |
| UMC156A and MMC0371 | Linkage to a preferred marker |
| UMC156A and UMC1702 | Linkage to a preferred marker |
| UMC1142 and UMC1299 | Linkage to a preferred marker |
| UMC1142 and BNLG1621A | Linkage to a preferred marker |
| UMC1142 and MMC0371 | Linkage to a preferred marker |
| UMC1142 and UMC1702 | Linkage to a preferred marker |
| UMC1346 and UMC1299 | Linkage to a preferred marker |
| UMC1346 and BNLG1621A | Linkage to a preferred marker |
| UMC1346 and MMC0371 | Linkage to a preferred marker |
| UMC1346 and UMC1702 | Linkage to a preferred marker |

Each of the intervals described above contains a clustering of markers that can co-segregate with GLS tolerance. This clustering of markers occurs in relatively small domains on the chromosome and can be linked to one or more QTL in those chromosome regions. QTL intervals were drawn to encompass the markers that co-segregate with tolerance. The intervals are defined by the markers on their termini, where the interval encompasses all the markers that map within the interval as well as the markers that define the termini.

In some cases, an interval may be defined by linkage to a preferred marker. For example, an interval on chromosome 4 is defined by any marker that is linked to the marker PHM 01811 within a certain distance, referencing any suitable genetic linkage map. For example, as used herein, linkage is defined as any marker that is within 25 cM of PHM 01811, as defined by the IBM2 2004 Neighbors map found on the MaizeGDB website. This interval on chromosome 4 is further illustrated in Table 3. These markers are shown in genetic order. Each of the markers listed, including the terminal markers BNLG1755 and UMC1299, are members of the interval. The BNLG1755 and UMC1299 markers are known in the art.

As described above, an interval (e.g., a chromosome interval or a QTL interval) need not depend on an absolute measure of interval size such as a centimorgan value. An interval can be described by the terminal markers that define the endpoints of the interval, and typically the interval will include the terminal markers that define the extent of the interval. For example, the physical map in FIG. 4 depicts the physical region of the chromosome bounded by and including PHM 00045 and PHM 00049. An interval can include any marker localizing within that chromosome domain, whether those markers are currently known or unknown. The invention provides a variety of means for defining a chromosome interval, for example, in the lists of linked markers of Table 3, and in references cited herein.

Genetic Maps

As one of skill in the art will recognize, recombination frequencies (and as a result, genetic map positions) in any particular population are not static. The genetic distances separating two markers (or a marker and a QTL) can vary depending on how the map positions are determined. Variables such as the parents selected, the mapping populations used, the software used in the marker mapping or QTL mapping, and the parameters input by the user of the mapping software can contribute to the QTL/marker genetic map relationships. For example, cM distances can very greatly depending on the number of recombination cycles used to create the mapping population (e.g., IBM2=eight recombination cycles, while BC1 herein is one recombination cycle; thus, the IBM2 distances of 5 cM are quite different from BC1 distances of 5 cM). However, it is not intended that the invention be limited to any particular mapping populations, use of any particular software, or any particular set of software parameters to determine linkage of a particular marker or chromosome interval with the GLS tolerance phenotype. It is well within the ability of one of ordinary skill in the art to extrapolate the novel features described herein to any maize gene pool or population of interest, using any particular software and software parameters. Indeed, observations regarding tolerance markers and chromosome intervals in populations in additions to those described herein are readily made using the teaching of the present disclosure.

Mapping Software

A variety of commercial software is available for genetic mapping and marker association studies (e.g., QTL mapping). This software includes but is not limited to software listed in Table 2.

TABLE 2

| Software | Description/References |
| --- | --- |
| Windows QTL Cartographer Version 2.5 | Wang S., C. J. Basten, and Z.-B. Zeng (2007). Windows QTL Cartographer 2.5. Department of Statistics, North Carolina State University, Raleigh, NC. |
| JoinMap ® | VanOoijen, and Voorrips (2001) "JoinMap 3.0 software for the calculation of genetic linkage maps", Plant Research International, Wageningen, the Netherlands; and, Stam "Construction of integrated genetic linkage maps by means of a new computer package: JoinMap", The Plant Journal 3(5): 739-744 (1993) |
| MapQTL ® | J. W. vanOoijen, "Software for the mapping of quantitative trait loci in experimental populations", Kyazma B. V., Wageningen, Netherlands |
| MapManager QT | Manly and Olson, "Overview of QTL mapping software and introduction to Map Manager QT", Mamm. Genome 10: 327-334 (1999) |
| MapManager QTX | Manly, Cudmore and Meer, "MapManager QTX, cross-platform software for genetic mapping", Mamm. Genome 12: 930-932 (2001) |
| GeneFlow ® and QTLocate ™ | GENEFLOW, Inc. (Alexandria, VA) |
| TASSEL | (Trait Analysis by aSSociation, Evolution, and Linkage) by Edward Buckler, and information about the program can be found on the Buckler Lab web page at the Institute for Genomic Diversity at Cornell University. |

Unified Genetic Maps

"Unified", "consensus", or "integrated" genetic maps have been created that incorporate mapping data from two or more sources, including sources that used different mapping populations and different modes of statistical analysis. The merging of genetic map information increases the marker density on the map. These improved maps can be advantageously used in marker assisted selection and map-based cloning and provide an improved framework for positioning newly identified molecular markers. The improved maps also aid in the identification of QTL chromosome intervals and clusters of advantageously-linked markers.

In some aspects, a consensus map is derived by simply overlaying one map on top of another. In other aspects, various algorithms, e.g., JoinMap® analysis, allows the combination of genetic mapping data from multiple sources, and reconciles discrepancies between mapping data from the original sources. See, Van Ooijen and Voorrips (2001) "JoinMap 3.0 software for the calculation of genetic linkage maps", Plant Research International, Wageningen, the Netherlands; Stam (1993) "Construction of integrated genetic linkage maps by means of a new computer package: JoinMap", The Plant Journal 3(5):739-744.

Linked Markers

From the present disclosure and widely recognized in the art, it is clear that any genetic marker that has a significant probability of co-segregation with a phenotypic trait of interest (e.g., in the present case, a newly conferred tolerance or enhanced tolerance trait) can be used as a marker for that trait. A list of useful QTL markers provided by the present invention is provided in FIG. 3.

In addition to the QTL markers noted in FIG. 3, additional markers linked to (showing linkage disequilibrium with) the QTL markers can also be used to predict the newly conferred tolerance or enhanced tolerance trait in a maize plant. In other words, any other marker showing less than 50% recombination frequency (separated by a genetic distance less than 50 cM) with a QTL marker of the invention (e.g., the markers provided in FIG. 3) is also a feature of the invention. Any marker that is linked to a QTL marker can also be used advantageously in marker-assisted selection for the particular trait.

Genetic markers that are linked to QTL (e.g., QTL markers provided in FIG. 3) are particularly useful when they are sufficiently closely linked to a given QTL that they display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be closely linked to each other.

In some aspects, linked markers (including closely linked markers) of the invention are determined by review of a genetic map, for example, the integrated genetic maps found on the MaizeGDB website. For example, it is shown herein that the linkage group 4 markers PHM 15534, PHM 04694, PHM 01811, PHM 01963, PHM 05013, and PHM 00586; and markers designed to bacb.pk0333.o19 (PHM 00043), bacc.pk0267.m12.f, cl33021_1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (PHM 00049) correlate with at least one GLS tolerance QTL. Markers that are linked to the aforementioned markers can be determined, for example, from Table 3.

TABLE 3

Markers within 25 cM of PHM 01811 on IBM2 2004 Neighbors map

| Marker | Map Position (IBM2 2004 Neighbors from MaizeGDB website) |
|---|---|
| BNLG1755 | 299.90 |
| UAZ73 | 300.09 |
| BNL35B (BLR) | 300.09 |
| CSU81B (ANK) | 300.11 |
| MPIK19B | 300.18 |
| UCSD72G | 300.19 |
| MMP45 | 300.20 |
| MPIK11D | 300.21 |
| IAS12 | 300.36 |
| NPI259A | 300.38 |
| UCSD64F | 300.38 |
| UMC23B | 300.46 |
| BNLG1930 | 300.46 |
| UMC156A | 301.16 |
| UAZ170 | 301.16 |
| UMC1142 | 302.50 |
| NPI340B | 304.16 |
| UMC1346 | 304.30 |
| UMC1702 | 305.20 |
| MMP155 | 305.50 |
| UAZ47A | 305.95 |
| MMP149A | 306.40 |
| UMC1299 | 306.42 |

Similarly, linked markers (including closely linked markers) of the invention can be determined by review of any suitable maize genetic map. For example, integrated genetic maps can be found on the MaizeGDB website resource.

It is not intended that the determination of linked or closely linked markers be limited to the use of any particular maize genetic map. Indeed, a large number of maize genetic maps is available and are well known to one of skill in the art. Alternatively, the determination of linked and closely linked markers can be made by the generation of an experimental dataset and linkage analysis.

It is also not intended that the identification of markers that are linked (e.g., within about 50 cM or within about 10 cM) to the GLS tolerance QTL markers identified herein be limited to any particular map or methodology. The integrated genetic maps provided on the MaizeGDB website serve only as example for identifying linked markers. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any maize genetic map can be used to determine markers that are linked and closely linked to the QTL markers of the present invention.

Techniques for Marker Detection

The invention provides molecular markers that have a significant probability of co-segregation with QTL that impart a GLS tolerance phenotype. These QTL markers find use in marker assisted selection for desired traits (newly conferred tolerance or enhanced tolerance), and also have other uses. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD"), cleaved amplified polymorphic sequences (CAPS), or amplified fragment length polymorphisms (AFLP)). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more properties of nucleic acids for their detection. For example, some techniques for detecting genetic markers utilize hybridization of a probe nucleic acid to nucleic acids corresponding to the genetic marker (e.g., amplified nucleic acids produced using genomic maize DNA as a template). Hybridization formats, including but not limited to solution phase, solid phase, mixed phase, or in situ hybridization assays, are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York; as well as in Sambrook and Ausubel (herein); and Berger and Kimmel, Guide to Molecular Cloning *Techniques, Methods in Enzymology volume* 152 Academic Press, Inc., San Diego, Calif. ("Berger").

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzymes that produce informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and calorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.) (Available on CD ROM).

Amplification-Based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also, Ausubel, Sambrook and Berger, above.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature, and MBs are available from a number of commercial reagent sources. See also, e.g., Leone et al. (1995) "Molecular beacon probes combined with amplification by NASBA enable homogenous real-time detection of RNA", *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" Science 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. Nos. 5,925,517, 6,150,097, and 6,037,130.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

Additional Details Regarding Amplified Variable Sequences, SSR, AFLP, ASH, SNPs and Isozyme Markers Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) *Nucleic Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection of large numbers of polymorphic markers and has been used for genetic mapping of plants (Becker et al. (1995) *Mol Gen Genet.* 249:65; and Meksem et al. (1995) *Mol Gen Genet.* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. This distinction can be detected by differential migration patterns of an amplicon comprising the SNP on, e.g., an acrylamide gel. Alternative modes of detection, such as hybridization, e.g., ASH, or RFLP analysis are also appropriate. SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp. 475-492; Shi (2001) Clin Chem 47, pp. 164-172; Kwok (2000) Pharmacogenomics 1, pp. 95-100; Bhattramakki and Rafalski (2001) Discovery and application of single nucleotide polymorphism markers in plants. In: R. J. Henry, Ed, Plant Genotyping: The DNA Fingerprinting of Plants, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), supra). Haplotypes can be more informative than single SNPs and can be more descriptive of any particular genotype. For example, a single SNP may be allele 'T' for PHM 01811-32, but the allele 'T' might also occur in the maize breeding population being utilized for recurrent parents. In this case, a haplotype, e.g. a series of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Isozyme markers can be employed as genetic markers, e.g., to track markers other than the tolerance markers herein, or to track isozyme markers linked to the markers herein. Isozymes are multiple forms of enzymes that differ from one another in their amino acid sequences, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qββ-replicase amplification and other RNA polymerase mediated techniques (e.g., NASBA), are found in the references noted above, e.g., Innis, Sambrook, Ausubel, Berger and Croy. Additional details are found in Mullis et al. (1987) U.S. Pat. No. 4,683,202; Arnheim & Levinson (Oct. 1, 1990) *C&EN* 36-47; *The Journal Of NIH Research* (1991) 3:81-94; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al. (1988) *Science* 241:1077-1080; Van Brunt (1990) *Biotechnology* 8:291-294; Wu and Wallace (1989) *Gene* 4: 560; Barringer et al. (1990) *Gene* 89:117; and Sooknanan and Malek (1995) *Biotechnology* 13:563-564. Improved methods of amplifying large nucleic acids by PCR, which is useful in the context of positional cloning, are further summarized in Cheng et al. (1994) *Nature* 369:684, and the references therein, in which PCR amplicons of up to 40 kb are generated.

Detection of Markers For Positional Cloning

In some embodiments, a nucleic acid probe is used to detect a nucleic acid that comprises a marker sequence. Such probes can be used, for example, in positional cloning to isolate nucleotide sequences linked to the marker nucleotide sequence. It is not intended that the nucleic acid probes of the invention be limited to any particular size. In some embodiments, a nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using autoradiography, fluorography or other similar detection techniques depending on the label to be detected. Examples of specific hybridization protocols are widely available in the art, see, e.g., Berger, Sambrook, and Ausubel, all herein.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.* 22(20): 1859-1862, e.g., using a commercially available automated synthesizer, e.g., as described in Needham-VanDevanter et al. (1984) *Nucleic Acids Res.* 12:6159-6168. Oligonucleotides, including modified oligonucleotides, can also be ordered from a variety of commercial sources known to persons of skill. There are many commercial providers of oligo synthesis services, and thus, this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.), and many others. Similarly, PNAs can be custom ordered from any of a variety of sources, such as PeptidoGenic, HTI Bio-Products, Inc., BMA Biomedicals Ltd (U.K.), Bio-Synthesis, Inc., and many others.

In Silico Marker Detection

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Amplification Primers for Marker Detection

In some preferred embodiments, the molecular markers of the invention are detected using a suitable PCR-based detection method, where the size or sequence of the PCR amplicon is indicative of the absence or presence of a particular marker allele. In these types of methods, PCR primers are hybridized to the conserved regions flanking the polymorphic marker region. As used in the art, PCR primers used to amplify a molecular marker are sometimes termed "PCR markers" or simply "markers".

It will be appreciated that, although many specific examples of primers are provided herein (see, e.g., FIG. 3, FIG. 9, and FIG. 10), suitable primers to be used with the invention can be designed using any suitable method. It is not intended that the invention be limited to any particular primer or primer pair. For example, primers can be designed using any suitable software program, such as LASERGENE®.

In some embodiments, the primers of the invention are radiolabelled, or labeled by any suitable means (e.g., using a non-radioactive fluorescent tag), to allow for rapid visualization of the different size amplicons following an amplification reaction and size separation, e.g. by electrophoresis on agarose gel. In some embodiments, the primers are not labeled, and the amplicons are visualized following their size resolution with, e.g., ethidium bromide staining.

It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype, to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly maize plants, that have newly conferred tolerance or enhanced tolerance to, or are susceptible to, GLS by identifying plants having a specified allele at one of those loci, e.g., PHM 15534, PHM 04694, PHM 01811, PHM 01963, PHM 05013, and PHM 00586; and markers designed to bacb.pk0333.o19 (PHM 00043), bacc.pk0267.m12.f, cl33021_1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (PHM 00049).

Similarly, by identifying plants lacking the desired marker locus, susceptible or less tolerant plants can be identified and, e.g., eliminated from subsequent crosses. Similarly, these marker loci can be introgressed into any desired genomic background, germplasm, plant, line, variety, etc., as part of an overall MAS breeding program designed to enhance maize yield.

The invention also provides chromosome QTL intervals that find equal use in MAS to select plants that demonstrate newly conferred or enhanced GLS tolerance. Similarly, the QTL intervals can also be used to counter-select plants that are susceptible or have reduced tolerance to GLS. Any marker that maps within the QTL interval (including the termini of the intervals) finds use with the invention. These intervals are defined by the following pairs of markers: (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702.

In general, MAS uses polymorphic markers that have been identified as having a significant likelihood of co-segregation with a tolerance trait. Such markers are presumed to map near a gene or genes that give the plant its tolerance phenotype, and are considered indicators for the desired trait, and are termed QTL markers. Plants are tested for the presence of a desired allele at the QTL marker. The most preferred markers (or marker alleles) are those that have the strongest association with the tolerance trait.

Linkage analysis is used to determine which polymorphic marker allele demonstrates a statistical likelihood of co-segregation with the tolerance phenotype (thus, a "tolerance marker allele"). Following the identification of a marker allele for co-segregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired tolerance phenotype. In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "*TECHNIQUES FOR MARKER DETECTION*". After the presence (or absence) of a particular marker allele in the biological sample is verified, the plant is selected (e.g., used to make progeny plants by selective breeding).

Maize plant breeders desire combinations of tolerance loci with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to tolerance loci, provide an effective method for selecting tolerant varieties in breeding programs. For example, one advantage of marker-assisted selection over field evaluations for tolerance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance to different diseases, the efficiency of MAS compared to phenotypic screening becomes even greater, because all the loci can be evaluated in the lab together from a single sample of DNA. In the present instance, the PHM 15534, PHM 04694, PHM 01811, PHM 01963, PHM 05013, and PHM 00586; and markers designed to bacb.pk0333.o19 (e.g., PHM 00043), bacc.pk0267.m12.f, cl33021_1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (e.g., PHM 00049) markers, as well as any of the chromosome intervals (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702, can be assayed simultaneously or sequentially from a single sample or a population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to GLS.

The presence and/or absence of a particular genetic marker or allele, e.g., PHM 15534, PHM 04694, PHM 01811, PHM 01963, PHM 05013, and PHM 00586; and markers designed to bacb.pk0333.o19 (e.g., PHM 00043), bacc.pk0267.m12.f, cl33021_1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (e.g., PHM 00049) markers, as well as any of the chromosome intervals (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702, in the genome of a plant is made by any method noted herein. If the nucleic acids from the plant are positive for a desired genetic marker allele, the plant can be self fertilized to create a true breeding line with the same genotype, or it can be crossed with a plant with the same marker or with other desired characteristics to create a sexually crossed hybrid generation.

Introgression of Favorable Alleles—Efficient Backcrossing of Tolerance Markers into Elite Lines One application of MAS, in the context of the present invention, is to use the newly conferred tolerance or enhanced tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of maize varieties with the desired complement (set) of allelic forms of chromosome segments associated with superior agronomic performance (tolerance, along with any other available markers for yield, etc.). Any of the disclosed marker alleles can be introduced into a maize line via introgression, by traditional breeding (or introduced via transformation, or both), to yield a maize plant with superior agronomic performance. The number of alleles associated with tolerance that can be introduced or be present in a maize plant of the present invention ranges from one to the number of alleles disclosed herein, each integer of which is incorporated herein as if explicitly recited.

The present invention also extends to a method of making a progeny maize plant and these progeny maize plants, per se. The method comprises crossing a first parent maize plant with a second maize plant and growing the female maize plant under plant growth conditions to yield maize plant progeny. Methods of crossing and growing maize plants are well within the ability of those of ordinary skill in the art. Such maize plant progeny can be assayed for alleles associated with tolerance and, thereby, the desired progeny selected. Such progeny plants or seed can be sold commercially for maize production, used for food, processed to obtain a desired constituent of the maize, or further utilized in subsequent rounds of breeding. At least one of the first or second maize plants is a maize plant of the present invention in that it comprises at least one of the allelic forms of the markers of the present invention, such that the progeny are capable of inheriting the allele.

A method of the present invention can be applied to at least one related maize plant such as from progenitor or descendant lines in the subject maize plant's pedigree such that inheritance of the desired tolerance allele can be traced. The number of generations separating the maize plants being subject to the methods of the present invention will generally be from 1 to 20, commonly 1 to 5, and typically 1, 2, or 3 generations of separation, and quite often a direct descendant or parent of the maize plant will be subject to the method (i.e., one generation of separation).

Introgression of Favorable Alleles—Incorporation of "Exotic" Germplasm while Maintaining Breeding Progress Genetic diversity is important for long term genetic gain in any breeding program. With limited diversity, genetic gain will eventually plateau when all the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite×exotic maize lines by subjecting the segregating progeny to MAS to maintain major yield alleles, along with the tolerance marker alleles herein.

Positional Cloning

The molecular marker loci and alleles of the present invention, e.g., PHM 15534, PHM 04694, PHM 01811, PHM 01963, PHM 05013, and PHM 00586; and markers designed to bacb.pk0333.o19 (e.g., PHM 00043), bacc.pk0267.m12.f, cl33021_1, bacb.pk0241.h17.f, chp2.pk0007.d2, p0094.csstg88, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18, bacb.pk0540.c18.f, and bacm.pk022.b8 (e.g., PHM 00049) markers, as well as any of the chromosome intervals (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702, can be used, as indicated previously, to identify a tolerance QTL, which can be cloned by well established procedures, e.g., as described in detail in Ausubel, Berger and Sambrook, herein.

These tolerance clones are first identified by their genetic linkage to markers of the present invention. Isolation of a nucleic acid of interest is achieved by any number of methods as discussed in detail in such references as Ausubel, Berger and Sambrook, herein, and Clark, Ed. (1997) *Plant Molecular Biology: A Laboratory Manual* Springer-Verlag, Berlin.

For example, "positional gene cloning" uses the proximity of a tolerance marker to physically define an isolated chromosomal fragment containing a tolerance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the ORF is identified by successive rounds of screening and isolation of clones which together comprise a contiguous sequence of DNA, a process termed "chromosome walking", resulting in a "contig" or "contig map". Protocols sufficient to guide one of skill through the isolation of clones associated with linked markers are found in, e.g., Berger, Sambrook and Ausubel, all herein.

Generation of Transgenic Cells and Plants

The present invention also relates to host cells and organisms which are transformed with nucleic acids corresponding to tolerance QTL identified according to the invention. For example, such nucleic acids include chromosome intervals (e.g., genomic fragments), ORFs and/or cDNAs that encode a newly conferred tolerance or enhanced tolerance trait. Additionally, the invention provides for the production of polypeptides that provide newly conferred tolerance or enhanced tolerance by recombinant techniques.

General texts which describe molecular biological techniques for the cloning and manipulation of nucleic acids and production of encoded polypeptides include Berger, Sambrook, and Ausubel supra. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors of this invention (e.g., vectors, such as expression vectors which comprise an ORF derived from or related to a tolerance QTL) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (From et al. (1985) *Proc. Natl. Acad. Sci. USA* 82:5824), infection by viral vectors such as cauliflower mosaic virus (CaMV) (Hohn et al. (1982) *Molecular Biology of Plant Tumors* (Academic Press, New York), pp. 549-560; U.S. Pat. No. 4,407,956), high velocity ballistic penetration by small particles with the nucleic acid either within the matrix of small beads or particles, or on the surface (Klein et al. (1987) *Nature* 327:70), use of pollen as vector (WO85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233:496; Fraley et al. (1983) *Proc. Natl. Acad. Sci. USA* 80:4803). Additional details regarding nucleic acid introduction methods are found in Sambrook, Berger and Ausubel, supra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, supra, plant regeneration from cultured protoplasts is described in Evans et al. (1983) "Protoplast Isolation and Culture", *Handbook of Plant Cell Cultures* 1, 124-176 (MacMillan Publishing Co.), New York; Davey (1983) "Recent Developments in the Culture and Regeneration of Plant Protoplasts", *Protoplasts, pp.* 12-29, (Birkhauser, Base1); Dale (1983) "Protoplast Culture and Plant Regeneration of Cereals and Other Recalcitrant Crops", *Protoplasts* pp. 31-41, (Birkhauser, Basel); Binding (1985) "Regeneration of Plants", *Plant Protoplasts*, pp. 21-73, (CRC Press, Boca Raton, Fla.). Additional details regarding plant cell culture and regeneration include Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture; Fundamental Methods* Springer Lab Manual, Springer-Verlag (Berlin Heidelberg New York) and *Plant Molecular Biology* (1993) R. R. D. Croy, Ed. Bios Scientific Publishers, Oxford, U.K. ISBN 0 12 198370 6. Cell culture media in general are also set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc. (St Louis, Mo.) ("Sigma-LSRCCC") and, e.g., *the Plant Culture Catalogue* and supplement (e.g., 1997 or later) also from Sigma-Aldrich, Inc. (St Louis, Mo.) ("Sigma-PCCS").

The present invention also relates to the production of transgenic organisms, which may be bacteria, yeast, fungi, animals or plants, transduced with the nucleic acids of the invention (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase, and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328: 731; Schneider et al. (1995) *Protein Expr. Purif.* 6:10; Ausubel, Sambrook, Berger (all supra). A catalogue of Bacteria and Bacteriophages useful for cloning is provided, e.g., by the American Type Culture Collection (ATCC), e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, N.Y. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Introducing Nucleic Acids into Plants.

Embodiments of the present invention pertain to the production of transgenic plants comprising the cloned nucleic acids, e.g., isolated ORFs and cDNAs encoding tolerance genes. Techniques for transforming plant cells with nucleic acids are widely available and can be readily adapted to the invention. In addition to Berger, Ausubel and Sambrook, all supra, useful general references for plant cell cloning, culture and regeneration include Jones (ed) (1995) *Plant Gene Transfer and Expression Protocols—Methods in Molecular Biology*, Volume 49 Humana Press Towata N.J. ("Jones"); Payne et al. (1992) *Plant Cell and Tissue Culture in Liquid Systems* John Wiley & Sons, Inc. New York, N.Y. ("Payne"); and Gamborg and Phillips (eds) (1995) *Plant Cell, Tissue and Organ Culture; Fundamental Methods* Springer Lab Manual, Springer-Verlag (Berlin Heidelberg New York) ("Gamborg"). A variety of cell culture media are described in Atlas and Parks (eds) *The Handbook of Microbiological Media* (1993) CRC Press, Boca Raton, Fla. ("Atlas"). Additional information for plant cell culture is found in available commercial literature such as the *Life Science Research Cell Culture Catalogue* (1998) from Sigma-Aldrich, Inc. (St Louis, Mo.) (Sigma-LSRCCC) and, e.g., the *Plant Culture Catalogue* and supplement (1997) also from Sigma-Aldrich, Inc. (St Louis, Mo.) (Sigma-PCCS). Additional details regarding plant cell culture are found in Croy.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids of the present invention can be introduced into plants according to any of a variety of techniques known in the art. Techniques for transforming a wide variety of higher plant species are also well known and described in widely available technical, scientific, and patent literature. See, for example, Weising et al. (1988) *Ann. Rev. Genet.* 22:421-477.

The DNA constructs of the invention, for example plasmids, phagemids, cosmids, phage, naked or variously conjugated-DNA polynucleotides (e.g., polylysine-conjugated DNA, peptide-conjugated DNA, liposome-conjugated DNA), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones, as well as in the other references noted herein and available in the literature.

For example, the introduction of DNA constructs using polyethylene glycol precipitation is described in Paszkowski et al., *EMBO J.* 3:2717 (1984). Electroporation techniques are described in Fromm et al., *Proc. Natl. Acad. Sci. USA* 82:5824 (1985). Ballistic transformation techniques are described in Klein et al., *Nature* 327:70-73 (1987). Additional details are found in Jones and Gamborg, supra, and in U.S. Pat. No. 5,990,387.

Alternatively, and in some cases preferably, *Agrobacterium*-mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; Fraley et al. (1984) *Proc. Natl. Acad. Sci. USA* 80:4803: and reviewed in Hansen and Chilton (1998) *Curr. Top. Microbiol. Immunol.* 240:21 and Das (1998) *Subcellular Biochemistry 29: Plant Microbe Interactions*, pp. 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, P W J Rigby, Ed., London, Academic Press; and Lichtenstein and Draper (1985) In: *DNA Cloning*, Vol. 11, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16), (2) liposome-mediated DNA uptake (see, e.g., Freeman et al. (1984) *Plant Cell Physiol.* 25:1353), and (3) the vortexing method (see, e.g., Kindle (1990) *Proc. Natl. Acad. Sci. (USA)* 87:1228).

DNA can also be introduced into plants by direct DNA transfer into pollen as described by Zhou et al. (1983) *Meth. Enzymol.* 101:433; D. Hess (1987) *Intern Rev. Cytol.* 107:367; Luo et al. (1988) *Plant Mol. Biol. Rep.* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Regeneration of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne; Fundamental Methods Springer Lab Manual, Springer-Verlag (Berlin Heidelberg New York); Evans et al. (1983) *Protoplasts Isolation and Culture, Handbook of Plant Cell Culture* pp. 124-176, Macmillian Publishing Company, New York; and Binding (1985) *Regeneration of Plants, Plant Proto lasts* pp. 21-73, CRC Press, Boca Raton. Regeneration can also be obtained from plant callus, explants, somatic embryos (Dandekar et al. (1989) *J. Tissue Cult. Meth.* 12:145; McGranahan et al. (1990) *Plant Cell Rep.* 8:512) organs, or parts thereof. Such regeneration techniques are described generally in Klee et al. (1987) *Ann. Rev. Plant Phys.* 38:467-486. Additional details are found in Payne and Jones, both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots, and growth of the plantlets in soil. These methods are adapted to the invention to produce transgenic plants bearing QTL and other genes isolated according to the methods of the invention.

In addition, the regeneration of plants containing polynucleotides of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci. (U.S.A.)* 80:4803. This procedure typically produces shoots within two to four weeks, and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide disease tolerance, as provided by the present invention, be limited to maize species. Indeed, it is contemplated that the polypeptides that provide the desired tolerance in maize can also provide such tolerance when transformed and expressed in other agronomically and horticulturally important species. For example, such species include: soybean, canola, alfalfa, wheat, sunflower, and sorghum.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. (1983) *Nature* 303:209. Viral promoters include the 35S and 19S RNA promoters of cauliflower mosaic virus. See, Odell et al. (1985) *Nature* 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosulforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton. For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like, are included in the invention, provided that these parts comprise cells comprising the isolated nucleic acid of the present invention. Progeny and variants, and mutants of the regenerated plants, are also included within the scope of the invention, provided that these parts comprise the introduced nucleic acid sequences.

Transgenic or introgressed plants expressing a polynucleotide of the present invention can be screened for transmission of the nucleic acid of the present invention by, for example, standard nucleic acid detection methods or by immunoblot protocols. Expression at the RNA level can be determined to identify and quantitate expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

One embodiment of the invention is a transgenic plant that is homozygous for the added heterologous nucleic acid; e.g., a transgenic plant that contains two added nucleic acid sequence copies, e.g., a gene at the same locus on each chromosome of a homologous chromosome pair. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide of the present invention relative to a control plant (e.g., a native, non-transgenic plant). Back-crossing to a parental plant and out-crossing with a non-transgenic plant can be used to introgress the heterologous nucleic acid into a selected background (e.g., an elite or exotic maize line).

Methods for Assessing and Producing GLS Tolerant Maize Plants

Experienced plant breeders can recognize tolerant maize plants in the field and can select the tolerant individuals or populations for breeding purposes or for propagation. In this context, the plant breeder recognizes "tolerant" and "non-tolerant", or "susceptible", maize plants.

Such plant breeding practitioners will appreciate that plant tolerance is a phenotypic spectrum consisting of extremes in tolerance and susceptibility as well as a continuum of intermediate tolerance phenotypes. Tolerance also varies due to environmental effects and the severity of pathogen infection. Evaluation of phenotypes using reproducible assays and tolerance scoring methods are of value to scientists who seek to identify genetic loci that impart tolerance, conduct marker assisted selection for tolerant populations, and breed tolerance traits into elite maize lines via introgression techniques, for example.

In contrast to fortuitous field observations that classify plants as either "tolerant" or "susceptible", various systems are known for scoring the degree of plant tolerance or susceptibility. These techniques can be applied to different fields at different times, and provide approximate tolerance scores that can be used to characterize a given strain regardless of growth conditions or location.

This invention also is directed to methods for producing a maize plant by crossing a first parent maize plant with a second parent maize plant wherein either the first or second parent maize plant is an inbred maize plant of the line PHJEP. Further, both first and second parent maize plants can come from the inbred maize line PHJEP. Still further, this invention also is directed to methods for producing an inbred maize line PHJEP-derived maize plant by crossing inbred maize line PHJEP with a second maize plant, growing the progeny seed, and repeating the crossing and growing steps with the inbred maize line PHJEP-derived plant 0 to 5 times. Thus, any such methods using the inbred maize line PHJEP are part of this invention: selfing, backcrosses, hybrid production, crosses to populations, and the like. All plants produced using inbred maize line PHJEP as a parent are within the scope of this invention, including plants derived from inbred maize line PHJEP. Advantageously, the inbred maize line is used in crosses with other, different, maize inbreds to produce first generation (F1) maize hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk and the like.

Duncan et al., Planta (1985) 165:322-332 reflects that 97% of the plants cultured that produced callus were capable of plant regeneration. Subsequent experiments with both inbreds and hybrids produced 91% regenerable callus that produced plants. In a further study in 1988, Songstad et al., in Plant Cell Reports (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," Maize for Biological Research (Plant Molecular Biology Association, Charlottesville, Va. 1982, at 367-372)

and in Duncan, et al., "The Production of Callus Capable of Plant Regeneration from Immature Embryos of Numerous *Zea Mays* Genotypes," 165 Planta 322-332 (1985). Thus, another aspect of this invention is to provide cells which upon growth and differentiation produce maize plants having the physiological and morphological characteristics of inbred line PHJEP.

The utility of inbred maize line PHJEP also extends to crosses with other species. Commonly, suitable species will be of the family Graminaceae, and especially of the genera *Zea, Tripsacum, Coix, Schierachne, Polytoca, Chionachne*, and *Trilobachne*, of the tribe Maydeae. Potentially suitable for crosses with PHJEP may be the various varieties of grain sorghum, *Sorghum bicolor* (L.) *Moench*.

Automated Detection/Correlation Systems of the Invention

In some embodiments, the present invention includes an automated system for detecting markers of the invention and/or correlating the markers with a desired phenotype (e.g., tolerance). Thus, a typical system can include a set of marker probes or primers configured to detect at least one favorable allele of one or more marker locus associated with newly conferred tolerance or enhanced tolerance to GLS. These probes or primers are configured to detect the marker alleles noted in the tables and examples herein, e.g., using any available allele detection format, e.g., solid or liquid phase array based detection, microfluidic-based sample detection, etc.

For example, in one embodiment, the marker locus is PHM 15534, PHM 04694, PHM 01811, PHM 01963, PHM 05013, and PHM 00586, or any combination thereof, as well as any of the chromosome intervals (i) BNLG1755 and UMC1299, (ii) BNLG1755 and BNLG1621A, (iii) BNLG1755 and MMC0371, (iv) BNLG1755 and UMC1702, (v) UMC156A and UMC1299, (vi) UMC156A and BNLG1621A, (vii) UMC156A and MMC0371, (viii) UMC156A and UMC1702, (ix) UMC1142 and UMC1299, (x) UMC1142 and BNLG1621A, (xi) UMC1142 and MMC0371, (xii) UMC1142 and UMC1702, (xiii) UMC1346 and UMC1299, (xiv) UMC1346 and BNLG1621A, (xv) UMC1346 and MMC0371, and (xvi) UMC1346 and UMC1702, or any combination thereof, and the probe set is configured to detect the locus.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scanns, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is especially preferred and is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable allele and the predicted newly conferred tolerance or enhanced tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the presence or absence of the favorable allele and predicted newly conferred tolerance or enhanced tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" in the context of this invention refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program", by which positive amplification or hybridization signals are recognized by the integrated system and attributed to individual samples as a genotype. Additional programs correlate the identity of individual samples with phenotypic values or marker alleles, e.g., statistical methods. In addition there are numerous C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems of the invention.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase), suitable for recording data in a computer readable medium is acceptable as a database in the context of the present invention. Data regarding genotype for one or more molecular markers, e.g., ASH, SSR, RFLP, RAPD, AFLP, SNP, CAPS, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like (for, e.g., selecting files, retrieving data, reviewing tables of maker information), and an output device (e.g., a monitor, a printer) for viewing or recovering the product of the statistical analysis.

Thus, in one aspect, the invention provides an integrated system comprising a computer or computer readable medium comprising a set of files and/or a database with at least one data set that corresponds to the marker alleles herein. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for molecular marker analysis of the present invention can thus include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of maize plants with favorable allelic forms of chromosome segments involved in agronomic performance (e.g., newly conferred tolerance or enhanced tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (e.g., Intel x86 or Pentium chip-compatible DOS™, OS2™, WINDOWS™, WINDOWS NT™, WINDOWS 95™, WINDOWS 97™, WINDOWS 2000™, WINDOWS XP™, or WINDOWS VISTA™ based machines), MACINTOSH™, LINUX, or UNIX based (e.g., SUN™ work station) computers.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Mapping a Large Effect QTL for GLS Tolerance

The GLS source of tolerance is uncommon in North American (NA) germplasm. To create an elite line for use as a donor source for GLS tolerance, the GLS tolerant line PH14T (U.S. Pat. No. 5,942,670) was crossed to PHN46 (U.S. Pat. No. 5,567,861) in order to generate an F1 population. Individuals of the F1 population were later backcrossed to PHN46 to generate a BC5 backcross population of approximately 190 individuals.

The F1 populations were phenotyped in the field for GLS tolerance. Marker data was collected on each progeny individual using SSR markers, with good genome coverage to generate a molecular marker map for the population. QTL analysis of the data from the F1 population identified a QTL for GLS tolerance on Chromosome 4, bin 5, between markers UMC1791 and UMC1346.

The BC5 population was also phenotyped in the field for GLS resistance. Marker data was collected on each progeny individual using SSR markers, with good genome coverage to generate a molecular marker map for the population. The BC5 mapping population confirmed the location of the QTL for GLS tolerance and more precisely identified the QTL for GLS tolerance as being closely linked to BNLG1755. This QTL showed a large and consistent effect, and explained 8-44% of the total phenotypic variation (Table 4).

TABLE 4

Single marker regression QTL mapping of GLS tolerance from BC5 Population (all markers on Chromosome 4)

| Marker | WN | R2 | D21C | R2 | WWDGTF | R2 | WN & NH | R2 | Average GLS | R2 |
|---|---|---|---|---|---|---|---|---|---|---|
| PHI079 | 0.000 | 6.3 | 0.000 | 2.9 | 0.000 | 1.9 | 0.000 | 5.6 | 0.000 | 1.9 |
| BNLG1937 | 0.000 | 13.7 | 0.000 | 8.4 | 0.000 | 1.1 | 0.000 | 9.5 | 0.000 | 1.1 |
| BNLG1265 | 0.000 | 20.1 | 0.000 | 11.1 | 0.000 | 6.7 | 0.000 | 17.9 | 0.000 | 6.7 |
| BNLG1755 | 0.000 | 44.4 | 0.000 | 7.5 | 0.000 | 10.2 | 0.000 | 25.9 | 0.000 | 10.2 |
| UMC1175 | 0.000 | 8.4 | 0.000 | 3.4 | 0.000 | 6.9 | 0.000 | 6.0 | 0.000 | 6.9 |
| BNLG1189 | 0.000 | 6.0 | 0.015 | 0.6 | 0.019 | 1.8 | 0.000 | 4.4 | 0.000 | 1.8 |

Example 2

Fine Mapping of the QTL for GLS Tolerance

The integrated genetic and physical map of maize was used to identify all BAC contigs located in the region. Low-copy BAC ends sequences and PHM markers from these contigs were used to develop CAPS markers. It was determined that bacm2.pk027.h10.f and bacm.pk098.d7 flank the GLS locus on one side, and bacm.pk022.b8 and PHM 7245 flank on the other side.

Example 3

Development of PHJEP

A progeny individual derived from the BC4 generation that had the QTL region, a phenotype most like PHN46, and a good resistance phenotype was selected. The individual was selfed to ensure a largely homozygous genome. The resulting inbred was designated PHJEP. The introgression of the GLS QTL resulted in a disease resistance score for PHJEP of 4 (on a scale of 1-9) compared to 1 or 2 for PHN46. FIG. 6 demonstrates the phenotypic difference between PHN46 and PH14T following inoculation with Cercospora zeae-maydis.

The QTL was further backcrossed into PHN46. A progeny individual derived from the BC7 (dose 8) generation was selected that had the newly defined QTL region and a smaller segment of donor in the region immediately flanking the QTL. The individual was selfed to ensure a largely homozygous genome. The resulting inbreds were coded PHW6N and PHW6M. These inbreds were found to have GLS tolerance levels equivalent to PH14T and PHJEP. Since PHJEP was developed first and did not exhibit linkage drag or other deleterious effects due to the QTL introgression, PHJEP was selected as the primary donor for the GLS tolerance QTL over PHW6N and PHW6M.

Example 4

Unique Haplotype in PHJEP

The tropical donor region in PH14T has SNP nucleotides A and A at PHM 00045-01 and PHM 00043-01, respectively. The recurrent parent PHN46 has nucleotides G and G at these same marker loci. Introgression of the GLS QTL from PH14T into PHN46 and subsequent selection for the QTL over multiple BC generations, while selecting for recurrent parent in the flanking region, resulted in a recombination just above the GLS QTL and the nucleotides in PHJEP being G (PHN46 allele) and A (PH14T allele) for PHM 00045-01 and PHM 00043-01, respectively. The GLS QTL is located near the centromere of chromosome 4 in a region with low recombination frequency. The recombination just above the GLS locus in PHJEP is considered to be a rare recombination event. In subsequent breeding populations between PHJEP and other inbreds, this nucleotide pattern, or haplotype, has been maintained. During multiple introgressions of PHJEP GLS donor region into elite materials, this recombination has been maintained. One haplotype that defines the rare recombination is: PHM 00045-01: G; PHM 00043-01: A; PHM 15534-13: A; PHM 04694-10: G; PHM 01811-32: T; PHM 01963-15: T; PHM 01963-22: C; PHM 05013-12: T; PHM 00586-10: T; and PHM 00049-01: A (see Table 5). A survey of public and proprietary inbreds determined that this haplotype is unique to PHJEP. This allelic combination is unique in Applicants' germplasm.

TABLE 5

Haplotypes for Inbreds PH14T, PHN46, and PHJEP in Chromosome 4 Region Containing the GLS QTL

| | PH14T | PHN46 | PHJEP |
|---|---|---|---|
| PHM 00045-01 | 1, 1 | 3, 3 | 3, 3 |
| PHM 00043-01 | 1, 1 | 3, 3 | 1, 1 |
| PHM 15534-13 | 1, 1 | 4, 4 | 1, 1 |
| PHM 04694-10 | 3, 3 | 4, 4 | 3, 3 |
| PHM 01811-32 | 4, 4 | 2, 2 | 4, 4 |
| PHM 01963-15 | 4, 4 | 2, 2 | 4, 4 |
| PHM 01963-22 | 2, 2 | 2, 2 | 2, 2 |
| PHM 05013-12 | 4, 4 | 4, 4 | 4, 4 |

TABLE 5-continued

Haplotypes for Inbreds PH14T, PHN46, and PHJEP in
Chromosome 4 Region Containing the GLS QTL

|  | PH14T | PHN46 | PHJEP |
|---|---|---|---|
| PHM 00586-10 | 4, 4 | 2, 2 | 4, 4 |
| PHM 00049-01 | 1, 1 | 4, 4 | 1, 1 |

1 = A,
2 = C,
3 = G,
4 = T

Example 5

GLS Analysis of PH14T, PHN46, and PHJEP

PH14T, PHN46, and PHJEP were grown at 4 locations with 8 reps per location. Maize plants were evaluated for GLS on a 1 to 9 scale, with one being "poor" and 9 being "good". The mean GLS scores, based on a scale of 1 to 9, for PH14T, PHN46, and PHJEP were 5.4, 3.6, and 5.3, respectively. Inbred PHJEP had a 1.5-fold increase in disease resistance (on a scale of 1-9) as compared to inbred PHN46, and this difference was significant at a p-value≦0.05. Inbred PHJEP and the GLS tolerant line PH14T had similar scores for GLS.

Example 6

Conversions of Other Elite Inbreds with PHJEP

PHJEP was used as a donor to convert over 40 different inbreds to have GLS resistance. Table 6 shows a comparison between three of these hybrids and three hybrids produced from non-PHJEP sources.

TABLE 6

| Exp Hybrid | Yield (bu/a) | Stagrn | GLFSPT |
|---|---|---|---|
| PHP38/PHJEP | 188.5 | 193 | 6 |
| PH705/PHJEP | 185.8 | 147 | 6 |
| PH05F/PHJEP | 178.1 | 166 | 7 |
| 3394 (PHP38/PHN46) | 155.9 | 79 | 3 |
| PH705/PHN46 | 155.7 | 70 | 5 |
| PH05F/PHN46 | 153.3 | 70 | 5 |
| CV % | 5.9 | 25.5 | 13.6 |
| SED between 2 entry means | 7 | 37 | 1 |
| Advantage | 29 ± 4.0 | 96 ± 19 | 2.0 ± 0.5 |

Yield (bu/a) is yield (bushels/acre), that is, yield of the grain at harvest by weight or volume (bushels) per unit area (acre) adjusted to 15% moisture. Stagrn is stay green, that is, the measure of plant health near the time of black layer formation (physiological maturity). A high score indicates better late-season plant health. GLFSPT is gray leaf spot, that is, a 1-9 visual rating indicating the resistance to gray leaf spot. A higher score indicates a higher resistance. CV % is the coefficient of variance (expressed as a percentage). SED is standard error of the difference.

Example 7

Use of the QTL to Select GLS Tolerant Plants

The SSR markers PHI026 [PHI079 or GPC1 or GAPC1 or NC005], LGI145183 [BNLG1937], LGI455751 [BNLG1265], LGI135263 [BNLG1755], EST337321 [UMC1175], LGI123864 [BNLG1189] and UMC1346 were used to select for the donor QTL region from PH14T during successive backcrossing. Phenotyping was also carried out in BC3 (270 individuals) and BC4 (110 individuals) generations so that the QTL could be further validated and the location further refined.

In the BC4 population the QTL was localized to a region defined by BNLG1755 and UMC1346 (FIG. 2); a distance of 4.4 cM on the IBM2 2004 neighbors map. The GLS QTL was found to explain 55.1% of the total phenotypic variation. The average phenotypic effect of the QTL was greater than 2 on the GLS disease scale of 1-9.

Example 8

Efficacy in Hybrids

PHJEP, PHW6N, PHW6M, and the near-isogenic inbred PHN46 lacking the GLS QTL were test crossed to PHP38, PH705, and PH05F. The resulting hybrids were compared in 16 yield test locations, with 3-4 replications per location. The locations focused on the eastern corn belt regions. Fourteen locations provided yield data and 13 locations provided GLS tolerance data. The GLS tolerant versions of the hybrids were found to have a consistent yield advantage and increased disease tolerance compared to the non-tolerant versions (Table 7). In Table 7, 3394 is the hybrid formed by the cross between inbreds PHP38 and PHN46.

TABLE 7

| Check Hybrid | Exp Hybrid | Exp Hybrid Yield Advantage (bu/a) | Reps | Exp Hybrid GLFSPT Advantage | Reps |
|---|---|---|---|---|---|
| 3394 | PHP38/PHJEP | 20.9 | 47 | 2.7 | 50 |
| 3394 | PHP38/PHW6N | 9.4 | 15 | 2.4 | 19 |
| 3394 | PHP38/PHW6M | 19.3 | 4 | 2.8 | 12 |
| PH705/PHN46 | PH705/PHJEP | 30.3 | 6 | 1.7 | 7 |
| PH705/PHN46 | PH705/PHW6M | 13.4 | 6 | 1.6 | 7 |
| PH705/PHN46 | PH705/PHW6N | 21.3 | 6 | 1.3 | 7 |
| PH05F/PHN46 | PH05F/PHJEP | 43.5 | 6 | 2.0 | 7 |
| PH05F/PHN46 | PH05F/PHW6N | 40.9 | 5 | 1.7 | 9 |
| PH05F/PHN46 | PH05F/PHW6M | 36.9 | 4 | 1.4 | 9 |

For example, hybrids with PHJEP had between 20.9 and 43.5 bu/acre yield advantage and 1.7-2.7 increase in disease resistance (on a scale of 1-9). FIG. 7 demonstrates the effect of the GLS QTL on hybrid resistance.

Example 9

Map Based Analysis of the GLS Tolerance QTL

The markers BNLG1755 and UMC1346 were used to identify the B73 contigs 4022, 4023 and 4024 underlying the QTL region. Three CAPs (Cleaved Amplified Polymorphism) markers were designed to BACs bacm.pk040.o17 (marker PHM 00045), bcb.pk0333.o19 (PHM 00043) and bacm.pk022.b8 (PHM 00049) by designing primers to the BAC end sequences and cleaving the resulting amplicons (see FIG. 3). The same BAC end sequences were used to design Invader SNP marker assays for application in high-throughput molecular breeding. A BC7 population of 4,464 RI individuals was generated, and the CAPs markers were used to identify progeny individuals with recombinants in the region.

These progeny were phenotyped for GLS resistance in the field and also selfed to generate further progeny and enable more accurate phenotyping. The combined marker and phenotypic data were used to localize the QTL to contig 4024. Additional markers were developed to BACs (bacm2.pk065.b22.f, bacc.pk0267.m12.f, bacb.pk0241.h17.f, chp2.pk0007.d2, bacc.pk0530.fl3.f, bacb.pk0269.n19, bacb.pk0009.b21.f, bacb.pk0117.i09.f, bacc.pk0280.n12, bacb.pk0219.j20, bacc.pk0132.b16.f, bacb.pk0221.o22, bacb.pk0544.j18 and bacb.pk0540.c18.f) and an EST overgo probe (cl33021_1) within this contig. These additional CAPs markers were used to aid in fine mapping and map based cloning.

During the process of fine mapping, a project was initiated to sequence ESTs and BACs within the QTL region using the high throughput 454 sequencing technology from Life Sciences. Twenty five overlapping B73 BAC clones covering the interval between bcb.pk0333.o19 and p0094.csstg88 were pooled and sequenced by 454 Life Sciences. Short sequence reads meant that the sequences could not be assembled to create a tiling path, but deep sequence sampling of the BAC clones (average 20× coverage) suggested that the region was fully sequenced. Sequence annotation failed to identify a sequence resembling a disease resistance gene in this interval.

During this period, additional CAPs markers within the region were used to further locate the QTL to a region between the EST cl33021_1 and the BAC end bacb.pk0009.b21.f. This is illustrated in Table 8 where the number of recombinants column describes the number of plants out of 4,464 progeny individuals that had a recombination between the corresponding marker and the QTL. Zero recombinants show that the marker is very close to the gene causing the phenotype such that recombination cannot break the tight linkage between the phenotype (and therefore the gene) and the marker. Zero recombinants out of 4,464 progeny represents a recombination distance of less than 0.02 cM.

TABLE 8

Fine mapping of GLS QTL with 4,464 progeny individuals and markers developed to BAC-end sequences

| BAC | Marker | Number of Recombinants |
|---|---|---|
| bacb.pk0333.o19 | PHM 00043 | 29 |
| bacc.pk0267.m12.f | | 4 |
| cl33021_1 | | 7 |
| bacb.pk0241.h17.f | | 0 |
| chp2.pk0007.d2 | | 0 |
| p0094.csstg88 | | 0 |
| bacb.pk0269.n19 | | 0 |
| Putative R gene | | |
| bacb.pk0009.b21.f | | 20 |
| bacb.pk0117.i09.f | | 20 |
| bacc.pk0280.n12 | | 23 |
| bacb.pk0219.j20 | | 25 |
| bacc.pk0132.b16.f | | 27 |
| bacb.pk0221.o22 | | 27 |
| bacb.pk0544.j18 | | 35 |
| bacb.pk0540.c18.f | | 35 |
| bacm.pk022.b8 | PHI 00049 | 39 |

Two additional BAC clones; bacb.pk0269.n19 and bacb.pk0009.b21.f, were sequenced using the double-stranded random shotgun approach (Bodenteich et al., In "Automated DNA sequencing and analysis techniques" (ed. Adams et al.), pp. 42-50, Academic Press, London, UK (1994)). Briefly, after each BAC was isolated via a double-acetate cleared lysate protocol, the clones were sheared by nebulization, and the resulting fragments were end-repaired and subcloned into pBluescript II SK(+). After transformation into DH-10B electro-competent *Escherichia coli* cells (InVitrogen) via electroporation, the colonies were picked with an automatic Q-Bot colony picker (Genetix) and stored at −80° C. in freezing media containing 6% glycerol and 100 µg/ml Ampicillin.

For sequencing, clones were recovered from archived glycerol cultures grown/frozen in 384-well freezing media plates and replicated with a sterile 384 pin replicator (Genetix) in 384-well microtiter plates containing LB+100 µg/ml Ampicillin (replicated plates). Plasmids were then isolated, using the Templiphi DNA sequencing template amplification kit method (Amersham Biosciences). Briefly, the Templiphi method uses bacteriophage φ29 DNA polymerase to amplify circular single-stranded or double-stranded DNA by isothermal rolling circle amplification (Dean et al., Genome Res. 11:1095-99 (2001); Nelson et al., Biotechniques 32:S44-S47 (2002); Reagin et al., J. Biomol. Tech. 14:143-148 (2003)). Cells were added to 5 µl of dilution buffer and partially lysed at 95° C. for 3 min to release the denatured template. 5 µl of Templiphi premix were then added to each sample, and the resulting reaction mixture was incubated at 30° C. for 16 hours, then at 65° C. for 10 min to inactivate the (p29 DNA polymerase activity. DNA quantification with the PicoGreen® dsDNA Quantitation Reagent (Molecular Probes) was performed after diluting the amplified samples 1:3 in distilled water. The amplified products were then denatured at 95° C. for 10 min and end-sequenced in 384-well plates, using vector-primed M13 oligonucleotides and the ABI BigDye version 3.1 Prism sequencing kit. After ethanol-based cleanup, cycle sequencing reaction products were resolved and detected on Perkin-Elmer ABI 3730xl automated sequencers, and individual sequences were assembled with the public domain Phred/Phrap/Consed package. While Phred reads DNA sequencing trace files, calls bases, assigns a quality value to each called base, and writes the base calls and quality values to output files, Phrap uses Phred-based sequencing files for assembling shotgun DNA sequence data (see the Laboratory of Phil Green website, Genome Sciences Department, University of Washington). Consed is a tool for viewing, editing, and finishing sequence assemblies generated with Phred and Phrap (Gordon et al., Genome Res. 8:195-202 (1998)). Contig order was viewed and confirmed with Exgap (A. Hua, University of Oklahoma, personal communication), a local graphic tool that uses pair read information to order contigs generated by Phred, Phrap, and Consed, and confirms the accuracy of the Phrap-based assembly.

The assembled sequence contained an annotated protein-coding gene resembling a putative R gene of the type classified as an LRR-like protein kinase. The annotated sequence is presented in SEQ ID NO:49 (with the translated amino acid sequence shown in SEQ ID NO:50). The CAPs marker for bacb.pk0269.n19 was found to preside in the 3' end of the putative R gene.

What is claimed is:

1. Maize variety PHJEP, representative seed of said maize variety having been deposited as ATCC accession number PTA-8851.

2. A seed of the maize variety of claim 1.

3. A plant of the maize variety of claim 1.

4. A plant cell of the plant of claim 3.

5. A maize seed produced by crossing the plant of claim 3 with a second maize plant, wherein said maize seed comprises a PHJEP gray leaf spot tolerance locus and that, when grown, produces a plant that exhibits gray leaf spot tolerance.

6. The maize seed of claim 5, wherein said PHJEP gray leaf spot tolerance locus comprises the chromosomal region of PHJEP defined by UMC1346 and UMC1702.

7. The maize seed of claim 5, wherein the PHJEP gray leaf spot tolerance locus is defined by a haplotype comprising:
   a. a G at PHM 00045-01;
   b. an A at PHM 00043-01;
   c. an A at PHM 15534-13;
   d. a G at PHM 04694-10;
   e. a T at PHM 01811-32;
   f. a T at PHM 01963-15;
   g. a C at PHM 01963-22;
   h. a T at PHM 05013-12;
   i. a T at PHM 00586-10; and
   j. an A at PHM 00049-01.

8. The maize seed of claim 5, wherein said PHJEP gray leaf spot tolerance locus is defined by a haplotype comprising:
   a. a G at PHM 00045-01;
   b. an A at PHM 00043-01;
   c. a C at PHM 01963-22; and
   d. a T at PHM 05013-12.

9. The maize seed of claim 5, wherein said maize seed is a backcross conversion of the PHJEP gray leaf spot tolerance locus.

10. The maize seed of claim 9, wherein the backcross conversion was produced with a recurrent parent selected from PHVNV, PHW3Y, PHVRA, PHEWB, and PHWRC.

11. The maize seed of claim 5, wherein the maize seed is a hybrid variety, and at least one inbred parent of said hybrid variety is a backcross conversion of the PHJEP gray leaf spot tolerance locus into a recurrent parent selected from PHVNV, PHW3Y, PHVRA, PHEWB, and PHWRC.

12. A maize plant produced by growing the maize seed of claim 5.

13. A plant cell of the maize plant of claim 12.

* * * * *